(12) United States Patent
Zhang et al.

(10) Patent No.: US 9,884,819 B2
(45) Date of Patent: Feb. 6, 2018

(54) TETRAHYDROCARBAZOLE INHIBITORS OF SIRT1 RECEPTORS

(71) Applicant: Auspex Pharmaceuticals, Inc., La Jolla, CA (US)

(72) Inventors: Chengzhi Zhang, San Diego, CA (US); Ralph Laufer, Tel Aviv (IL)

(73) Assignee: Auspex Pharmaceuticals, Inc., Frazer, PA (US)

( * ) Notice: Subject to any disclaimer, the term of this patent is extended or adjusted under 35 U.S.C. 154(b) by 0 days.

(21) Appl. No.: 15/400,144

(22) Filed: Jan. 6, 2017

(65) Prior Publication Data

US 2017/0190664 A1 Jul. 6, 2017

Related U.S. Application Data

(60) Provisional application No. 62/275,444, filed on Jan. 6, 2016.

(51) Int. Cl.
| | |
|---|---|
| *C07D 209/86* | (2006.01) |
| *A61K 45/06* | (2006.01) |
| *A61K 31/403* | (2006.01) |
| *A61K 31/4704* | (2006.01) |

(52) U.S. Cl.
CPC .......... *C07D 209/86* (2013.01); *A61K 31/403* (2013.01); *A61K 31/4704* (2013.01); *A61K 45/06* (2013.01)

(58) Field of Classification Search
CPC .................................................. C07D 209/86
See application file for complete search history.

(56) References Cited

U.S. PATENT DOCUMENTS

| 8,785,492 B2 | 7/2014 | Dressman et al. |
| 2005/0256181 A1 | 11/2005 | Distefano |

FOREIGN PATENT DOCUMENTS

WO   WO 2007/047604   4/2007

OTHER PUBLICATIONS

Huntington's Disease [online], retrieved from the internet on Mar. 6, 2017, URL: http://www.mayoclinic.org/diseases-conditions/huntingtons-disease/basics/definition/CON-20030685.*
Foster "Deuterium Isotope Effects in the Metabolism of Drugs and Xenobiotics: Implications for Drug Design", Advances in Drug Research, Academic Press, London, vol. 14, pp. 1-40, Jan. 1985.
Ko et al., "In Vitro Inhibition of Cytochrome P450 (CYP450) system by the Antiplatelet Drug Ticlopidine: Potent Effect on CYP2C19 and CYP2D6" British Journal of Clinical Pharmacology; 49, pp. 343-351, 2000.
Kumari et al., "Sirtuin Inhibition Induces Apoptosis-like Changes in Platelets and Thrombocytopenia" Journal of Biological Chemistry, vol. 290, No. 19, pp. 12290-12299, May 2015.
Lim et al., "SirT1 Deacetylates RORyt and Enhances Th17 Cell Generation", The Journal of Experimental Medicine, vol. 212, No. 5, pp. 607-617, May 2015.
Singh et al., "Expression/Localization Patterns of Sirtuins (SirT1, SirT2, and SirT7) During Progression of Cervical Cancer and effects of Sirtuin Inhibitors on Growth of Cervical Cancer Cells", Tumor Biology, vol. 36, Issue 8, pp. 6159-6171, Aug. 2015.
Sussmuth et al., "An Exploratory Double-Blind, Randomized Clinical Trial With Selisistat, a SirT1 Inhibitor, in Patients with Huntington's Disease" British Journal of Clinical Pharmacology, vol. 79, No. 3, pp. 465-476, Mar. 2015.
Uebelhack et al., "Inhibition of Platelet MAO-B by Kava Pyrone-Enriched Extract from Piper Methysticum Forster (Kava-Kava)", Pharmacopsychiatry, vol. 31, pp. 187-192, Sep. 1998.
Vachharajani et al., "Preclinical Pharmacokinetics and Metabolism of BMS-214778, a Novel melatonin Receptor Agonist", vol. 92, Issue 4, pp. 760-772, Apr. 2003.

(Continued)

*Primary Examiner* — Shawquia Jackson
(74) *Attorney, Agent, or Firm* — Baker & Hostetler LLP

(57) ABSTRACT

Described are deuterium-substituted tetrahydrocarbazole compounds of Formulae I, II, or III which are inhibitors of sirtuin 1 (SIRT1). Also described are pharmaceutical compositions comprising the deuterium-substituted tetrahydrocarbazole compounds, and methods of use thereof.

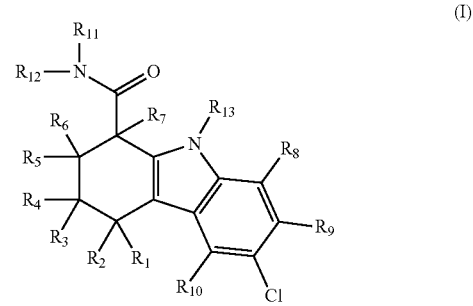

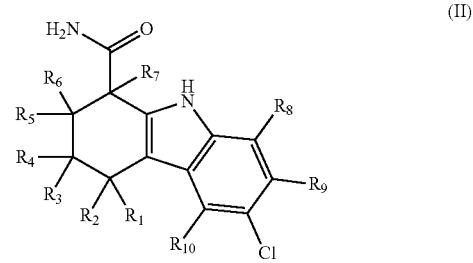

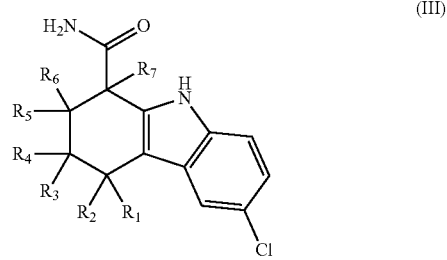

14 Claims, No Drawings

(56) References Cited

OTHER PUBLICATIONS

Westerberg et al., Safety, Pharmacokinetics, Pharmacogenomics and QT Concentration-effect Modelling of the SirT1 Inhibitor Selisistat in Healthy Volunteers; British Journal of Clinical Pharmacology, vol. 79, No. 3, pp. 477-491, Mar. 2015.

Weyler et al., "Purification and Properties of Mitochondrial Monoamine Oxidase Type A from Human Placenta", The Journal of Biological Chemistry, vol. 260, No. 24, pp. 13199-13207, Oct. 1985.

* cited by examiner

TETRAHYDROCARBAZOLE INHIBITORS OF SIRT1 RECEPTORS

CROSS-REFERENCE TO RELATED APPLICATIONS

This application claims the benefit of the priority of U.S. Provisional Patent Application No. 62/275,444, filed Jan. 6, 2016, the disclosure of which is hereby incorporated by reference in its entirety.

TECHNICAL FIELD

Disclosed herein are new tetrahydrocarbazole compounds and compositions and their application as pharmaceuticals for the treatment of disorders. Methods of inhibition of SirT1 activity in a subject are also provided for the treatment of disorders such Huntington's disease.

BACKGROUND

Selisistat (6-chloro-2,3,4,9-tetrahydro-1H-carbazole-1-carboxamide) is a sirtuin 1 (SIRT1) inhibitor. Sirtuins are evolutionarily conserved NAD(+)-dependent acetyl-lysine deacetylases that belong to class III type histone deacetylases, and play critical roles in transcriptional regulation, cell cycling, replicative senescence, inflammation, and metabolism.

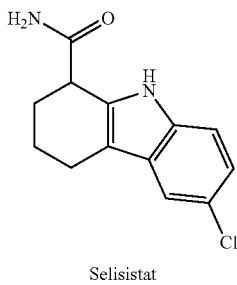 [SMILES: NC(=O)C1CCCc2c1[nH]c1ccc(Cl)cc21]

Selisistat

Selisistat is currently under investigation for the treatment of neurodegenerative diseases such as Huntington's disease. See, e.g., Seussmuth et al., British Journal of Clinical Pharmacology (2015), 79(3), 465-476. Huntington's disease (HD) is a monogenetic, autosomal dominant neurodegenerative disease characterized by symptoms such as chorea, dystonia, behavioral disturbances, cognitive decline, and dementia. The disease is caused by an increase in the length of a CAG (cytosine, adenine, guanine) triplet repeat, encoding for the amino acid glutamine, present in the N-terminal part of the 'Huntington gene' ('huntingtin', HTT). SIRT1 is one of the few deacetylases capable of deacetylating mutant HTT. Inhibition of SIRT1 results in increased acetylation of specific lysine residues of the mutant protein, which increases the rate of autophagocytic clearance selectively of the mutant HTT protein. Selisistat has been shown to increase acetylation at specific lysine residues of mutant HTT in cell models, resulting in an increased rate of macroautophagic clearance of the mutant protein, and is neuroprotective in both the drosophila model of HD, and in a transgenic r6/2 mouse model, where it showed statistically significant effects on life span and several psychomotor and histological endpoints. Furthermore, a recent clinical trial demonstrated that selisistat appears to be safe and well-tolerated in human subjects. See Westerberg Get al., Br J Clin Pharmacol. 2015, 79(3):477-91. No disease-modifying treatment for Huntington's disease is yet available, and current therapy is directed at symptoms associated with the disease. Selisistat therefore represents a promising therapy for Huntington's disease.

Selisistat has also shown promise in treating autoimmune disorders such as multiple sclerosis. SIRT1 acts an epigenetic regulator that modulates the activity of several transcription factors important for immune function. Though first understood to have a primarily antiinflammatory function, more recent work focusing on T cells has identified an important proinflammatory action as a negative regulator of T reg cell function. SIRT1 promotes autoimmunity by deacetylating RORγt, the signature transcription factor of Th17 cells, increasing RORγt transcriptional activity, and enhancing Th17 cell generation and function. Both T cell—specific SIRT1 deletion and treatment with pharmacologic SIRT1 inhibitors suppress Th17 differentiation and are protective in a mouse model of multiple sclerosis. See, e.g., Lim et al., J Exp Med, (2015), 212(5), 607-617.

Selisistat has also shown promise in treating thrombosis and cancer. See, e.g., Kumari et al., J Biol Chem (2015), 290(19), 12290-12299; Singh et al., Tumor Biol (2015), 36(8), 6159-6171.

Selisistat is, however, subject to $CYP_{450}$-mediated oxidative metabolism, including hydroxylation of the cyclohexyl group and oxidative deamination, followed by glucuronic acid conjugation across all species studied (mouse, rat, dog, human). A phenotyping study in vitro showed that CYP3A4 and CYP1A2 were the major isoforms involved in the formation of the hydroxylated metabolites while CYP2D6 and CYP2C19 play a minor role. Elimination of selisistat occurs in a biphasic manner, with an apparent terminal plasma half-life that appears to increase with dose, and suggested that one or more clearance mechanisms approach saturation at higher doses. Furthermore, in the multi-dose contingents of the study, the observed fraction of the dose excreted in the urine increased with time, consistent with plasma accumulation. Intersubject variability (% CV) was also observed: in the single-dose phase, 35-71% (56% average) in $AUC_{(0,\infty)}$ and 23-46% (33% average) in $C_{max}$, with similar variability in the multiple-dose phase. Females experiences higher drug exposure and a higher incidence of adverse effects (e.g., headache and gastrointestinal complaints).

Accordingly, there still exists a need in the art for SIRT1 inhibitors, and derivatives of selisistat, with improved pharmacologic properties.

SUMMARY

Provided are deuterium-substituted tetrahydrocarbazole compounds, which are sirtuin 1 (SIRT1) inhibitors. Also provided are pharmaceutical compositions comprising the deuterium-substituted tetrahydrocarbazole compounds, and methods of use thereof, including methods for treating SIRT1-mediated disorders by administering, to a patient, the deuterium-substituted tetrahydrocarbazole compounds or pharmaceutical compositions comprising the deuterium-substituted tetrahydrocarbazole compounds. Further provided are methods of synthesizing the deuterium-substituted tetrahydrocarbazole compounds.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

Deuterium Kinetic Isotope Effect

In order to eliminate foreign substances such as therapeutic agents, the animal body expresses various enzymes, such as the cytochrome $P_{450}$ enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C—C) π-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k=Ae^{-Eact/RT}$. The Arrhenius equation states that, at a given temperature, the rate of a chemical reaction depends exponentially on the activation energy ($E_{act}$).

The transition state in a reaction is a short lived state along the reaction pathway during which the original bonds have stretched to their limit. By definition, the activation energy $E_{act}$ for a reaction is the energy required to reach the transition state of that reaction. Once the transition state is reached, the molecules can either revert to the original reactants, or form new bonds giving rise to reaction products. A catalyst facilitates a reaction process by lowering the activation energy leading to a transition state. Enzymes are examples of biological catalysts.

Carbon-hydrogen bond strength is directly proportional to the absolute value of the ground-state vibrational energy of the bond. This vibrational energy depends on the mass of the atoms that form the bond, and increases as the mass of one or both of the atoms making the bond increases. Since deuterium (D) has twice the mass of protium ($^1H$), a C-D bond is stronger than the corresponding C—$^1H$ bond. If a C—$^1H$ bond is broken during a rate-determining step in a chemical reaction (i.e. the step with the highest transition state energy), then substituting a deuterium for that protium will cause a decrease in the reaction rate. This phenomenon is known as the Deuterium Kinetic Isotope Effect (DKIE). The magnitude of the DKIE can be expressed as the ratio between the rates of a given reaction in which a C—$^1H$ bond is broken, and the same reaction where deuterium is substituted for protium. The DKIE can range from about 1 (no isotope effect) to very large numbers, such as 50 or more. Substitution of tritium for hydrogen results in yet a stronger bond than deuterium and gives numerically larger isotope effects Deuterium ($^2H$ or D) is a stable and non-radioactive isotope of hydrogen which has approximately twice the mass of protium ($^1H$), the most common isotope of hydrogen. Deuterium oxide ($D_2O$ or "heavy water") looks and tastes like $H_2O$, but has different physical properties.

When pure $D_2O$ is given to rodents, it is readily absorbed. The quantity of deuterium required to induce toxicity is extremely high. When about 0-15% of the body water has been replaced by $D_2O$, animals are healthy but are unable to gain weight as fast as the control (untreated) group. When about 15-20% of the body water has been replaced with $D_2O$, the animals become excitable. When about 20-25% of the body water has been replaced with $D_2O$, the animals become so excitable that they go into frequent convulsions when stimulated. Skin lesions, ulcers on the paws and muzzles, and necrosis of the tails appear. The animals also become very aggressive. When about 30% of the body water has been replaced with $D_2O$, the animals refuse to eat and become comatose. Their body weight drops sharply and their metabolic rates drop far below normal, with death occurring at about 30 to about 35% replacement with $D_2O$. The effects are reversible unless more than thirty percent of the previous body weight has been lost due to $D_2O$. Studies have also shown that the use of $D_2O$ can delay the growth of cancer cells and enhance the cytotoxicity of certain antineoplastic agents.

Deuteration of pharmaceuticals to improve pharmacokinetics (PK), pharmacodynamics (PD), and toxicity profiles has been demonstrated previously with some classes of drugs. For example, the DKIE was used to decrease the hepatotoxicity of halothane, presumably by limiting the production of reactive species such as trifluoroacetyl chloride. However, this method may not be applicable to all drug classes. For example, deuterium incorporation can lead to metabolic switching. Metabolic switching occurs when xenogens, sequestered by Phase I enzymes, bind transiently and re-bind in a variety of conformations prior to the chemical reaction (e.g., oxidation). Metabolic switching is enabled by the relatively vast size of binding pockets in many Phase I enzymes and the promiscuous nature of many metabolic reactions. Metabolic switching can lead to different proportions of known metabolites as well as altogether new metabolites. This new metabolic profile may impart more or less toxicity. Such pitfalls are non-obvious and are not predictable a priori for any drug class.

Selisistat is a SIRT1 inhibitor. The carbon-hydrogen bonds of selisistat contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per $10^{18}$ protium atoms). Increased levels of deuterium incorporation may produce a detectable Deuterium Kinetic Isotope Effect (DKIE) that could affect the pharmacokinetic, pharmacologic and/or toxicologic profiles of such selisistat in comparison with the compound having naturally occurring levels of deuterium.

Based on discoveries made in our laboratory, as well as considering the literature, selisistat is likely metabolized in humans at the 1, 2, 3, and 4 positions of the cyclohexyl group. The current approach has the potential to prevent metabolism at these sites. Other sites on the molecule may also undergo transformations leading to metabolites with as-yet-unknown pharmacology/toxicology. Limiting the production of these metabolites has the potential to decrease the danger of the administration of such drugs and may even allow increased dosage and/or increased efficacy. All of these transformations can occur through polymorphically-expressed enzymes, exacerbating interpatient variability. Further, some disorders are best treated when the subject is medicated around the clock or for an extended period of time. For all of the foregoing reasons, a medicine with a longer half-life may result in greater efficacy and cost savings. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. The deuteration approach has the strong potential to slow the metabolism of selisistat and attenuate interpatient variability.

Novel compounds and pharmaceutical compositions, certain of which have been found to inhibit SIRT1 have been discovered, together with methods of synthesizing and using the compounds, including methods for the treatment of SIRT1-mediated disorders in a patient by administering the compounds.

Provided herein are compounds of Formula I:

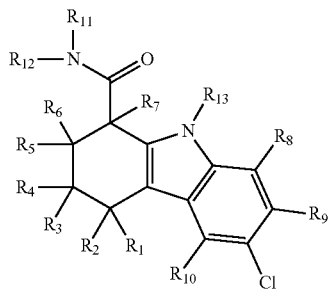

(I)

or a salt, prodrug, or solvate thereof, wherein:
$R_1$-$R_{13}$ are, independently, hydrogen or deuterium; and
at least one of $R_1$-$R_{13}$ is deuterium.

In some embodiments, $R_1$-$R_6$ are deuterium in the compounds of Formula I. In other embodiments, $R_7$ is deuterium in the compounds of Formula I. In further embodiments, $R_1$-$R_7$ are deuterium in the compounds of Formula I.

Certain compounds disclosed herein may possess useful SIRT1-inhibiting activity, and may be used in the treatment or prophylaxis of a disorder in which SIRT1 and/or histone acetylation play an active role. Thus, certain embodiments also provide pharmaceutical compositions comprising one or more compounds disclosed herein together with a pharmaceutically acceptable carrier, as well as methods of making and using the compounds and compositions. Certain embodiments provide methods for inhibiting SIRT1. Other embodiments provide methods for treating a SIRT1-mediated disorder in a patient in need of such treatment, comprising administering to the patient a therapeutically effective amount of a compound or composition according to the present disclosure. Also provided is the use of certain compounds disclosed herein for use in the manufacture of a medicament for the prevention or treatment of a disorder ameliorated by the inhibition of SIRT1 and/or histone acetylation.

In certain embodiments of the present disclosure, the compounds have the structure of Formula II:

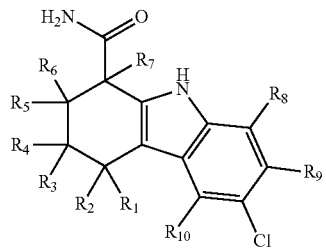

(II)

or a salt, prodrug, or solvate thereof, wherein:
$R_1$-$R_{10}$ are, independently, hydrogen or deuterium; and
at least one of $R_1$-$R_{19}$ is deuterium.

In certain embodiments, $R_1$ and $R_2$ are deuterium.
In certain embodiments, $R_1$, $R_2$, and $R_7$ are deuterium.
In certain embodiments, $R_3$, $R_4$, $R_5$, and $R_6$ are deuterium.
In certain embodiments, $R_3$, $R_4$, $R_5$, and $R_6$ are deuterium.
In certain embodiments, $R_3$, $R_4$, $R_5$, $R_6$, and $R_7$ are deuterium.
In further embodiments, $R_1$, $R_2$, $R_3$, $R_4$, $R_5$, and $R_6$ are deuterium.
In certain embodiments, $R_1$, $R_2$, $R_3$, $R_4$, $R_5$, $R_6$, and $R_7$ are deuterium.
In certain embodiments, $R_7$ is deuterium.

Also provided herein are embodiments according to each of the embodiments above, wherein $R_8$, $R_9$, and $R_{10}$ are deuterium.

Also provided herein are embodiments according to each of the embodiments above, wherein every other substituent among $R_1$-$R_{10}$ not specified as deuterium is hydrogen.

In certain embodiments, at least one of $R_1$-$R_{10}$ which is deuterium has deuterium enrichment of no less than about 1%. In certain embodiments, at least one of $R_1$-$R_{10}$ which is deuterium has deuterium enrichment of no less than about 10%. In certain embodiments, at least one of $R_1$-$R_{10}$ which is deuterium has deuterium enrichment of no less than about 50%. In certain embodiments, at least one of $R_1$-$R_{10}$ which is deuterium has deuterium enrichment of no less than about 90%. In certain embodiments, at least one of $R_1$-$R_{10}$ which is deuterium has deuterium enrichment of no less than about 98%.

In certain embodiments of the present disclosure, the compounds have Formula III:

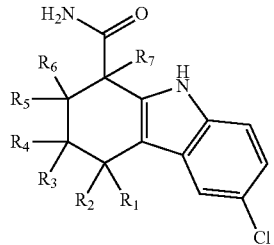

(III)

or a salt, prodrug, or solvate thereof, wherein:
$R_1$-$R_7$ are, independently, hydrogen or deuterium; and
at least one of $R_1$-$R_7$ is deuterium.
In certain embodiments, $R_1$ and $R_2$ are deuterium.
In certain embodiments, $R_1$, $R_2$, and $R_7$ are deuterium.
In certain embodiments, $R_3$, $R_4$, $R_5$, and $R_6$ are deuterium.
In certain embodiments, $R_3$, $R_4$, $R_5$, and $R_6$ are deuterium.

In certain embodiments, $R_3$, $R_4$, $R_5$, $R_6$, and $R_7$ are deuterium.

In further embodiments, $R_1$, $R_2$, $R_3$, $R_4$, $R_5$, and $R_6$ are deuterium In certain embodiments, $R_1$, $R_2$, $R_3$, $R_4$, $R_5$, $R_6$, and $R_7$ are deuterium.

In certain embodiments, $R_7$ is deuterium.

Also provided herein are embodiments according to each of the embodiments above, wherein every other substituent among $R_1$-$R_7$ not specified as deuterium is hydrogen.

In certain embodiments, at least one of $R_1$-$R_7$ which is deuterium has deuterium enrichment of no less than about 1%. In certain embodiments, at least one of $R_1$-$R_7$ which is deuterium has deuterium enrichment of no less than about 10%. In certain embodiments, at least one of $R_1$-$R_7$ which is deuterium has deuterium enrichment of no less than about 50%. In certain embodiments, at least one of $R_1$-$R_7$ which is deuterium has deuterium enrichment of no less than about 90%. In certain embodiments, at least one of $R_1$-$R_7$ which is deuterium has deuterium enrichment of no less than about 98%.

In certain embodiments, the compound is:

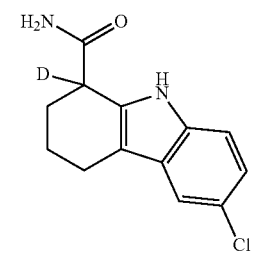 [SMILES: [2H]C1(C(N)=O)CCCc2c1[nH]c1ccc(Cl)cc21]

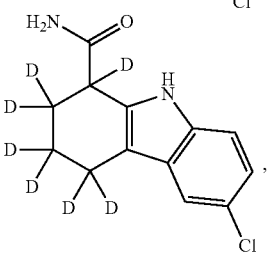

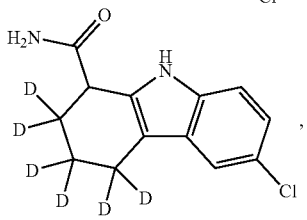

or a salt, prodrug, or solvate thereof.

In some embodiments, the compound is:

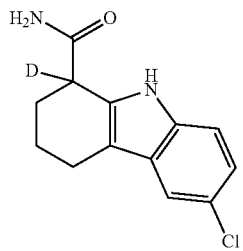

or a stereoisomer thereof, or a salt, prodrug, or solvate thereof. For example, the compound can be:

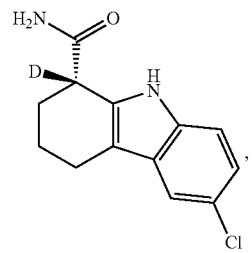

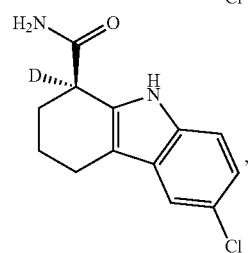

or a mixture thereof.

In some embodiments, the compound is:

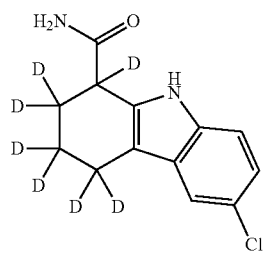 [SMILES: [2H]C1([2H])c2c([nH]c3ccc(Cl)cc23)C([2H])(C(N)=O)C([2H])([2H])C1([2H])[2H]]

or a stereoisomer thereof, or a salt, prodrug, or solvate thereof. For Example, the compound can be

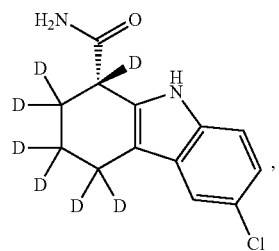

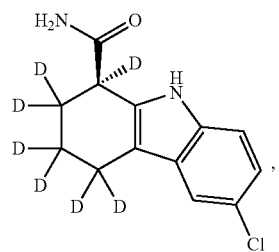

or a mixture thereof.

In some embodiments, the compound is:

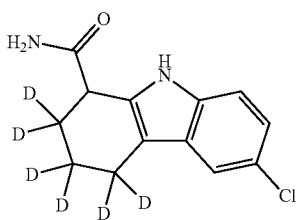 [SMILES: [2H]C1([2H])c2c([nH]c3ccc(Cl)cc23)C(C(N)=O)C([2H])([2H])C1([2H])[2H]]

or a stereoisomer thereof, or a salt, prodrug, or solvate thereof. For example, the compound can be

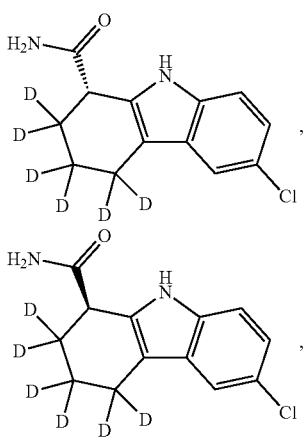

or a mixture thereof.

In certain embodiments, each position represented as D has deuterium enrichment of no less than about 1%. In certain embodiments, each position represented as D has deuterium enrichment of no less than about 10%. In certain embodiments, each position represented as D has deuterium enrichment of no less than about 50%. In certain embodiments, each position represented as D has deuterium enrichment of no less than about 90%. In certain embodiments, each position represented as D has deuterium enrichment of no less than about 98%.

The compounds as disclosed herein may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

In certain embodiments, the compound disclosed herein may expose a patient to a maximum of about 0.000005% $D_2O$ or about 0.00001% DHO, assuming that all of the C-D bonds in the compound as disclosed herein are metabolized and released as $D_2O$ or DHO. In certain embodiments, the levels of $D_2O$ shown to cause toxicity in animals is much greater than even the maximum limit of exposure caused by administration of the deuterium enriched compound as disclosed herein. Thus, in certain embodiments, the deuterium-enriched compound disclosed herein should not cause any additional toxicity due to the formation of $D_2O$ or DHO upon drug metabolism.

In certain embodiments, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

Also provided is a pharmaceutical composition comprising a compound as disclosed herein together with a pharmaceutically acceptable carrier.

Also provided is a method of treatment of a SIRT1-mediated disorder comprising the administration of a therapeutically effective amount of a compound as disclosed herein to a patient in need thereof.

In certain embodiments, the disorder is Huntington's disease.

In certain embodiments, the method of treatment of a SIRT1-mediated disorder further comprises the administration of an additional therapeutic agent.

In certain embodiments, the additional therapeutic agent is a drug for the treatment of abnormal involuntary movement or a movement disorder, an antipsychotic, an antidepressant, or a mood stabilizer.

In certain embodiments, the disorder is autoimmune disease.

In certain embodiments, autoimmune disease is multiple sclerosis.

In certain embodiments, administration of a therapeutically effective amount of a compound as disclosed herein to a patient with multiple sclerosis will ameliorate the occurrence of exacerbation (also known as relapse). In certain embodiments, administration of a therapeutically effective amount of a compound as disclosed herein to a patient with multiple sclerosis will ameliorate and/or reduce the progression of disability as measured by multiple clinical assessment instruments including but not limited to the EDSS, MSFC and its individual sub scores, cognitive assessments as detailed in the BICAMS, and other measures disclosed herein and known to those of skill in the art. In certain embodiments, administration of a therapeutically effective amount of a compound as disclosed herein to a patient with multiple sclerosis will ameliorate the formation and accumulation of CNS lesions associated with relapsing remitting and progressive forms of multiple sclerosis. In certain embodiments, administration of a therapeutically effective amount of a compound as disclosed herein to a patient with multiple sclerosis will ameliorate the atrophy of the brain and the spinal cord. In certain embodiments, administration of a therapeutically effective amount of a compound as disclosed herein to a patient with multiple sclerosis will improve the recovery of lesions as measured by MRI.

In certain embodiments, the disorder is inflammatory disease.

In certain embodiments, the method of treatment of a SIRT1-mediated disorder further results in at least one effect which is:
a) decreased inter-individual variation in plasma levels of the compound or a metabolite thereof as compared to the non-isotopically enriched compound;
b) increased average plasma levels of the compound per dosage unit thereof as compared to the non-isotopically enriched compound;
c) decreased average plasma levels of at least one metabolite of the compound per dosage unit thereof as compared to the non-isotopically enriched compound;
d) increased average plasma levels of at least one metabolite of the compound per dosage unit thereof as compared to the non-isotopically enriched compound; or e) an improved clinical effect during the treatment in the subject per dosage unit thereof as compared to the non-isotopically enriched compound.

In certain embodiments, the method of treatment of a SIRT1-mediated disorder further results in at least two effects which are:
a) decreased inter-individual variation in plasma levels of the compound or a metabolite thereof as compared to the non-isotopically enriched compound;
b) increased average plasma levels of the compound per dosage unit thereof as compared to the non-isotopically enriched compound;
c) decreased average plasma levels of at least one metabolite of the compound per dosage unit thereof as compared to the non-isotopically enriched compound;
d) increased average plasma levels of at least one metabolite of the compound per dosage unit thereof as compared to the non-isotopically enriched compound; or
e) an improved clinical effect during the treatment in the subject per dosage unit thereof as compared to the non-isotopically enriched compound.

In certain embodiments, the method effects a decreased metabolism of the compound per dosage unit thereof by at least one polymorphically-expressed cytochrome $P_{450}$ isoform in the subject, as compared to the corresponding non-isotopically enriched compound.

In certain embodiments, the cytochrome $P_{450}$ isoform is CYP2C8, CYP2C9, CYP2C19, or CYP2D6.

In certain embodiments, the compound is characterized by decreased inhibition of at least one cytochrome $P_{450}$ or monoamine oxidase isoform in the subject per dosage unit thereof as compared to the non-isotopically enriched compound.

In certain embodiments, the cytochrome $P_{450}$ or monoamine oxidase isoform is CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, CYP51, $MAO_A$, or $MAO_B$.

In certain embodiments, the method reduces a deleterious change in a diagnostic hepatobiliary function endpoint, as compared to the corresponding non-isotopically enriched compound.

In certain embodiments, the diagnostic hepatobiliary function endpoint is alanine aminotransferase ("ALT"), serum glutamic-pyruvic transaminase ("SGPT"), aspartate aminotransferase ("AST," "SGOT"), ALT/AST ratios, serum aldolase, alkaline phosphatase ("ALP"), ammonia levels, bilirubin, gamma-glutamyl transpeptidase ("GGTP," "γ-GTP," "GGT"), leucine aminopeptidase ("LAP"), liver biopsy, liver ultrasonography, liver nuclear scan, 5'-nucleotidase, or blood protein.

Also provided is a compound as disclosed herein for use as a medicament.

Also provided is a compound as disclosed herein for use in the manufacture of a medicament for the prevention or treatment of a disorder ameliorated by the inhibition of SIRT1.

As used herein, the terms below have the meanings indicated.

The singular forms "a," "an," and "the" may refer to plural articles unless specifically stated otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ ... to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium," when used to describe a given position in a molecule such as $R_1$-$R_{13}$ or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, in another no less than about 95%, in another no less than about 97%, in another no less than about 98%, or in another no less than about 99% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disorder" as used herein is intended to be generally synonymous, and is used interchangeably with, the terms "disease" and "condition" (as in medical condition), in that all reflect an abnormal condition of the human or animal body or of one of its parts that impairs normal functioning, is typically manifested by distinguishing signs and symptoms.

The terms "treat," "treating," and "treatment" are meant to include alleviating or abrogating a disorder or one or more of the symptoms associated with a disorder; or alleviating or eradicating the cause(s) of the disorder itself. As used herein, reference to "treatment" of a disorder is intended to include prevention. The terms "prevent," "preventing," and "prevention" refer to a method of delaying or precluding the onset of a disorder; and/or its attendant symptoms, barring a subject from acquiring a disorder or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The term "combination therapy" means the administration of two or more therapeutic agents to treat a therapeutic disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the disorders described herein.

The term "SIRT1-mediated disorder," refers to a disorder that is characterized by abnormal activity or expression of SIRT1, that, when inhibited, leads to the amelioration of other abnormal biological processes. A SIRT1-mediated disorder may be completely or partially mediated by modulating melatonin receptors. In particular, a SIRT1-mediated disorder is one in which inhibition of SIRT1 results in some effect on the underlying disorder, i.e., administration of a SIRT1 inhibitor results in some improvement in at least some of the patients being treated.

An inhibitor may fully or partially, and competitively or noncompetitively, inhibit SIRT1 and SIRT1 activity, depending on the concentration of the compound. Such inhibition may be contingent on the occurrence of a specific event, and/or may be manifest only in particular cell types. The term "SIRT1 inhibitor" or "inhibition of SIRT1" also refers to altering the function of SIRT receptor by decreasing the probability that a complex forms between an SIRT1 and a natural binding partner. In some embodiments, inhibition of SIRT1 may be assessed using commercially available SIRT1 activity assays such as those described below.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenecity, are commensurate with a reasonable benefit/risk ratio, and are effective for their intended use.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio.

The terms "active ingredient," "active compound," and "active substance" refer to a compound, which is administered, alone or in combination with one or more pharmaceutically acceptable excipients or carriers, to a subject for treating, preventing, or ameliorating one or more symptoms of a disorder.

The terms "drug," "therapeutic agent," and "chemotherapeutic agent" refer to a compound, or a pharmaceutical composition thereof, which is administered to a subject for treating, preventing, or ameliorating one or more symptoms of a disorder.

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "prodrug" refers to a compound functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. Examples of prodrugs may be prepared according to, e.g., "Design of Prodrugs", ed. H. Bundgaard, Elsevier, 1985. In some embodiments, the prodrug is an ester.

The compounds disclosed herein can exist as therapeutically acceptable salts. The term "therapeutically acceptable salt," as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

While it may be possible for the compounds of the subject disclosure to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art.

The compositions include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The compositions may conveniently be presented in unit dosage form and may be prepared by any of the methods well known in the art of pharmacy. Typically, these methods include the step of bringing into association a compound of the subject disclosure or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

For administration by inhalation, compounds may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Disclosed herein are methods of treating a SIRT1-mediated disorder comprising administering to a subject having or suspected to have such a disorder, a therapeutically effective amount of a compound as disclosed herein or a pharmaceutically acceptable salt, solvate, or prodrug thereof.

SirT1 receptor-mediated disorders, include, but are not limited to: neurodegenerative diseases such as Huntington's disease; autoimmune disorders such as multiple sclerosis; thrombosis; cancer; and/or any disorder which can lessened, alleviated, or prevented by administering a SIRT1 receptor modulator.

In certain embodiments, a method of treating a SIRT1-mediated disorder comprises administering to the subject a therapeutically effective amount of a compound of as disclosed herein, or a pharmaceutically acceptable salt, solvate, or prodrug thereof, so as to affect: (1) decreased inter-individual variation in plasma levels of the compound or a metabolite thereof; (2) increased average plasma levels of the compound or decreased average plasma levels of at least one metabolite of the compound per dosage unit; (3) decreased inhibition of, and/or metabolism by at least one cytochrome $P_{450}$ or monoamine oxidase isoform in the subject; (4) decreased metabolism via at least one polymorphically-expressed cytochrome $P_{450}$ isoform in the subject; (5) at least one statistically-significantly improved disorder-control and/or disorder-eradication endpoint; (6) an improved clinical effect during the treatment of the disorder, (7) prevention of recurrence, or delay of decline or appearance, of abnormal alimentary or hepatic parameters as the primary clinical benefit, or (8) reduction or elimination of deleterious changes in any diagnostic hepatobiliary function endpoints, as compared to the corresponding non-isotopically enriched compound.

In certain embodiments, inter-individual variation in plasma levels of the compounds as disclosed herein, or metabolites thereof, is decreased; average plasma levels of the compound as disclosed herein are increased; average plasma levels of a metabolite of the compound as disclosed herein are decreased; inhibition of a cytochrome $P_{450}$ or monoamine oxidase isoform by a compound as disclosed herein is decreased; or metabolism of the compound as disclosed herein by at least one polymorphically-expressed cytochrome $P_{450}$ isoform is decreased; by greater than about 5%, greater than about 10%, greater than about 20%, greater than about 30%, greater than about 40%, or by greater than about 50% as compared to the corresponding non-isotopically enriched compound.

Plasma levels of the compound as disclosed herein, or metabolites thereof, may be measured using the methods described in Vachharajani et al., J. Pharm. Sci., 2003, 92(4), 760-772 and U.S. Pat. No. 8,785,492, which are hereby incorporated by reference.

Examples of cytochrome $P_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, $MAO_A$, and $MAO_B$.

The inhibition of the cytochrome $P_{450}$ isoform is measured by the method of Ko et al. (*British Journal of Clinical Pharmacology*, 2000, 49, 343-351). The inhibition of the $MAO_A$ isoform is measured by the method of Weyler et al. (*J. Biol Chem.* 1985, 260, 13199-13207). The inhibition of the $MAO_B$ isoform is measured by the method of Uebelhack et al. (*Pharmacopsychiatry*, 1998, 31, 187-192).

Examples of polymorphically-expressed cytochrome $P_{450}$ isoforms in a mammalian subject include, but are not limited to, CYP2C8, CYP2C9, CYP2C19, and CYP2D6.

The metabolic activities of liver microsomes, cytochrome $P_{450}$ isoforms, and monoamine oxidase isoforms are measured by the methods described herein.

Examples of improved disorder-control and/or disorder-eradication endpoints, or improved clinical effects include, but are not limited to, reduction in the progression of, or reduction in one or more symptoms or indicators of:

Huntington's disease, for example
  a. improved Unified Huntington's Disease Rating Scale (UHDRS) scores;
  b. improved Total Maximal Chorea (TMC) Scores of the UHDRS;
  c. improved Total Motor Scores (TMS) of the UHDRS;
  d. improved Patient Global Impression of Change (PGIC) scores;
  e. improved Clinical Global Impression of Change (CGIC) scores;
  f. improved Abnormal Involuntary Movement Scale (AIMS) scores;
  g. improved Berg Balance Test scores;
  h. improved Physical Functioning Scale of the SF-36 scores; and
  i. improved Swallowing Disturbance Questionnaire (SDQ) scores;

Multiple sclerosis, For Example
  a. improved Expanded Disability Status Scale (EDSS) score;
  b. reduced time to confirmed disability progression as measured by EDSS or a sub scale thereof;
  c. improved Multiple Sclerosis Functional Composite (MSFC) score;
  d. improved cognitive assessments as detailed in the Brief International Cognitive Assessment for Multiple Sclerosis (BICAMS) or one of its assessments (i.e., Symbol Digit Modalities Test, California Verbal Learning Test, Brief Visuospatial Memory Test);
  e. reduced occurrence of relapse, for example as measured by annualized relapse rate and/or time to first or second relapse;
  f. reduction in new, enlarged, or reappearing lesions, or reduction in lesion volume;
  g. improved recovery of lesions (e.g., as measured by MRI);
  h. lessened reduction in body weight;
  i. lessened reduction in brain volume (typically at a longer time point, e.g., 2 years), or reduction in atrophy of the brain and/or the spinal cord;
  j. improved Patient Global Impression of Change (PGIC) scores; and
  k. improved Clinical Global Impression of Change (CGIC) scores.

Additional disorder-control and/or disorder-eradication endpoints for a given disease will be known to those in the art.

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", 4$^{th}$ edition, Mosby, 1999. These assays are run by accredited laboratories according to standard protocol.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Combination Therapy

The compounds disclosed herein may also be combined or used in combination with other agents useful in the treatment of SIRT1-mediated disorders, Huntington's disease and multiple sclerosis. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In certain embodiments, the compounds disclosed herein can be combined or co-administered with one or more VMAT2 inhibitors (vesicular monoamine transporter 2 inhibitors).

In certain embodiments, the compounds disclosed herein can be combined or co-administered with one or more drugs for the treatment of abnormal involuntary movements and/or movement disorders, such as tetrabenazine, deutetrabenazine, or laquinimod.

In certain embodiments, the compounds disclosed herein can be combined or co-administered with one or more drugs for the treatment of multiple sclerosis (and other neuroinflammatory/autoimmune/demyelinating diseases). Such drugs include: sphingosine 1-phosphate (S1P) receptor modulators such as fingolimod; immunomodulators such as teriflunomide, glatiramer acetate, mitoxantrone, and laquinimod; interferons such as interferon-1-beta; as well as relevant monoclonal antibodies such as natalizumab, which targets α4-integrin and reduces T-cell transmission to the CNS. In certain embodiments, the drug is laquinimod, which has been shown to cause aTh1 (T helper 1 cell, produces pro-inflammatory cytokines) to Th2 (T helper 2 cell, produces anti-inflammatory cytokines) shift with an anti-inflammatory profile; such an approach would complement the Th-17 modulation of selisistat.

In certain embodiments, the compounds disclosed herein can be combined with one or more antipsychotics chosen from chlorpromazine, fluphenazine, perphenazine, prochlorperazine, thioridazine, trifluoperazine, haloperidol, haloperidol decanoate, droperidol, pimozide, amisulpride, aripiprazole, bifeprunox, clozapine, melperone, norclozapine, olanzapine, risperidone, paliperidone, quetapine, symbyax, tetrabenazine, o ziprazidone.

In certain embodiments, the compounds disclosed herein can be combined or co-administered with one or more antidepressants chosen from amitriptyline, bupropion, citalopram, clomipramine, dapoxetine, desipramine, dothiepin, duloxetine, escitalopram, fluoxetine, fluvoxamine, imipramine, iofepramine, nortriptyline, paroxetine, protriptyline, sertraline, trazodone, trimipramine, or venlafaxine.

In certain embodiments, the compounds disclosed herein can be combined or co-administered with one or more mood-stabilizing drugs such as valproate, carbamazepine, or lamotrigine.

The compounds disclosed herein can also be administered in combination with other classes of compounds, including, but not limited to, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothlazide, hydrochiorothiazide, flumethiazide, hydroflumethiazide, bendroflumethiazide, methylchlorothiazide, trichlormethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiazolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/ antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Thus, in another aspect, certain embodiments provide methods for treating SIRT1-mediated disorders in a human or animal subject in need of such treatment comprising administering to the subject an amount of a compound disclosed herein effective to reduce or prevent the disorder in the subject, in combination with at least one additional agent for the treatment of the disorder that is known in the art. In a related aspect, certain embodiments provide therapeutic compositions comprising at least one compound disclosed herein in combination with one or more additional agents for the treatment of SIRT1-mediated disorders.

General Synthetic Methods for Preparing Compounds

Isotopic hydrogen can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

The compounds as disclosed herein can be prepared by methods known to one of skill in the art and routine modifications thereof, and/or following procedures similar to those described in the Example section herein and routine modifications thereof, and/or procedures found in US2005/0256181, which is hereby incorporated in their entirety, and references cited therein and routine modifications thereof. Compounds as disclosed herein can also be prepared as shown in any of the following schemes and routine modifications thereof.

The following schemes can be used to practice the present disclosure. Any position shown as hydrogen may optionally be replaced with deuterium.

Scheme I

Deuterated derivatives of selisistat may be prepared as shown below, wherein each R, each R', and each R'' is independently hydrogen or deuterium, provided that at least one R, R', or R'' is deuterium.

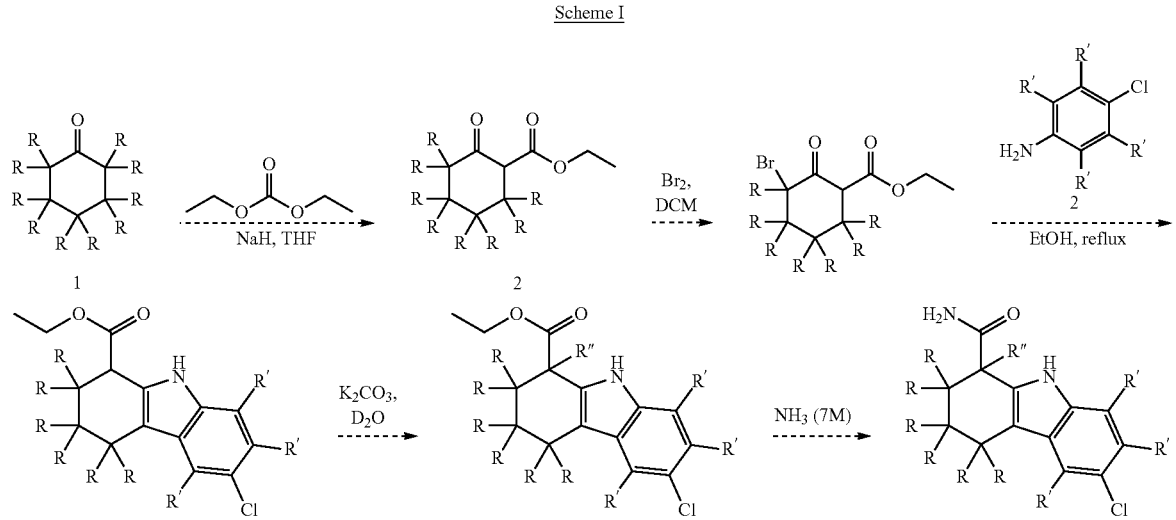

Scheme I

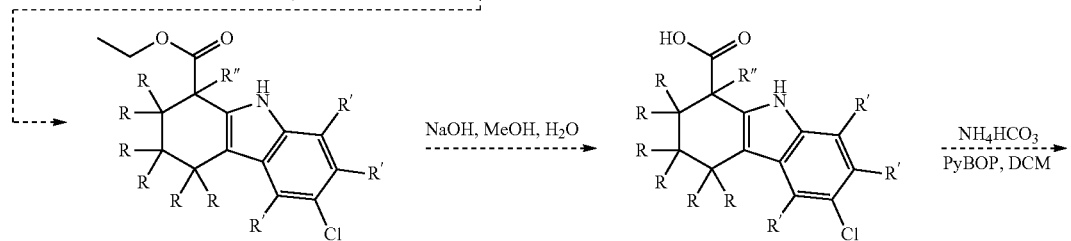

Scheme II

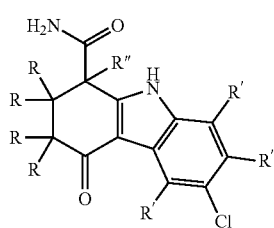
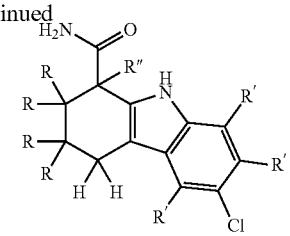

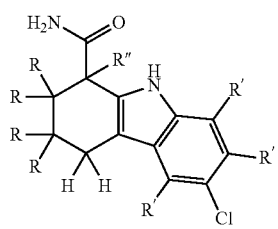

Deuterium can be incorporated to different positions synthetically, according to the synthetic procedures as shown in Scheme I, by using appropriate deuterated intermediates and reagents. For example, to introduce deuterium at one or more R positions, compound 1 with the corresponding deuterium substitutions (e.g., deuterated cyclohexanones such as $d_{10}$-cyclohexanone, 3,3,4,4,5,5-$d_6$-cyclohexanone, and 2,2,6,6-$d_4$-cyclohexanone) can be used. To introduce deuterium at one or more R' positions, compound 2 with the corresponding deuterium substitutions (e.g., deuterated chloroanilines such as 2,3,5,6-tetradeutero-4-chloroaniline) can be used. Alternatively, where one or more of R is hydrogen, deuterium may be introduced at one or more R positions using lithium aluminum deuteride or lithium borodeuteride (Scheme 2). Deuterium gas can also be used where appropriate.

Deuterium can be incorporated to various positions having an exchangeable proton, such as an amine N—H, via proton-deuterium equilibrium exchange.

The disclosure is now described with reference to the following examples. Before describing several exemplary embodiments of the disclosure, it is to be understood that the disclosure is not limited to the details of construction or process steps set forth in the following description. The disclosure is capable of other embodiments and of being practiced or being carried out in various ways.

The following abbreviations may be employed in the Examples and elsewhere herein:

DMA=dimethylacetamide
DMF=dimethylformamide
DMSO=dimethyl sulfoxide
DCM=dichloromethane
DBU=1,8-diazabicyloundec-7-ene
THF=tetrahydrofuran
TEA=triethylamine
LDA=lithium diisopropylamide
IBX=2-iodoxy benzoic acid
TosCl=4-toluene sulfonyl chloride
TBAC=tert-butyl acetate
L=liter
mL=milliliter
µL=microliter
g=gram(s)
mg=milligram(s)
mol=moles
mmol=millimole(s)
h or hr=hour(s)
min=minute(s)
Equiv=equivalent(s)
$H_2$=hydrogen
Ar=argon
$N_2$=nitrogen
RT or R.T.=room temperature
AT=ambient temperature
Aq.=aqueous
HPLC=high performance liquid chromatography
HPLC R,=HPLC retention time
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point All IUPAC names were generated using PerkinElmer®'s ChemDraw.

EXAMPLES

Example 1

Comparative: 6-chloro-2,3,4,9-tetrahydro-1H-carbazole-1-carboxamide (selisistat)

Selisistat was prepared as below, and may also be prepared as disclosed in U.S. 2005/0256181.

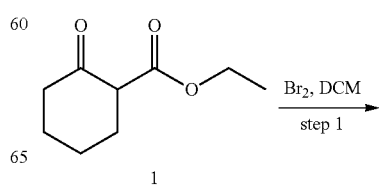

-continued

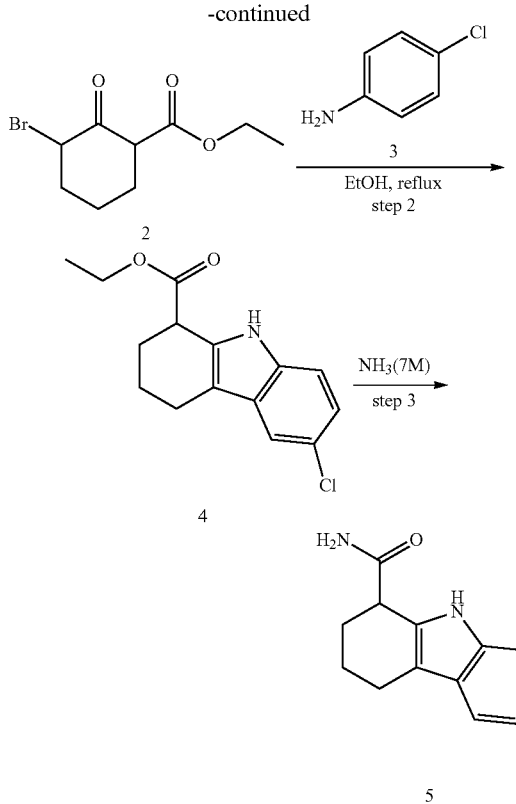

Step 1: To a solution of ethyl 2-oxocyclohexane-1-carboxylate (5 g, 29.38 mmol, 1.00 equiv) in dichloromethane (50 mL) was added Br$_2$ (4.7 g, 29.41 mmol, 1.00 equiv) dropwise with stirring at 0-5° C. over 30 min. The resulting solution was stirred for 3 h at 0° C. The reaction was then quenched by the addition of sodium carbonate (50 mL). The resulting solution was extracted with ethyl acetate (3×50 mL). The organic layers were combined and washed with water (3×30 mL) and brine (3×30 mL). The mixture was dried over anhydrous sodium sulfate and concentrated under vacuum to afford 7.2 g (98%) of ethyl 3-bromo-2-oxocyclohexane-1-carboxylate as yellow oil.

$^1$H NMR (400 MHz, CDCl$_3$) δ:12.10 (s, 1H), 4.70 (m, 1H), 4.33-4.07 (m, 2H), 2.54-1.71 (m, 6H), 1.37-1.17 (m, 3H).

Step 2: Ethyl 3-bromo-2-oxocyclohexane-1-carboxylate (2 g, 8.03 mmol, 1.00 equiv) (step 1) and 4-chloroaniline (2.55 g, 19.99 mmol, 2.50 equiv) were added into a 8-mL sealed tube. The resulting solution was stirred for 3 h at 150° C. The reaction mixture was cooled to 20° C. The reaction was diluted with ethyl acetate (50 mL). The solids were filtered out. The filtrate was washed with water (3×20 mL) and brine (3×20 mL). The organic layers were dried over anhydrous sodium sulfate and concentrated under vacuum. The residue was applied onto a silica gel column with ethyl acetate/petroleum ether (1:9) to afford 1.45 g (65%) of ethyl 6-chloro-2,3,4,9-tetrahydro$^1$H-carbazole-1-carboxylate as a yellow solid.

$^1$H NMR (400 MHz, CDCl$_3$) δ: 8.48 (s, 1H), 7.46-7.21 (m, 2H), 7.16-7.10 (m, 1H), 4.33-4.13 (m, 2H), 3.86 (m, 1H), 2.70 (m, 2H), 2.28-2.05 (m, 3H), 1.92-1.77 (m, 1H), 1.37-1.20 (m, 3H).

Step 3: Ethyl 6-chloro-2,3,4,9-tetrahydro-$^1$H-carbazole-1-carboxylate (1 g, 3.60 mmol, 1.00 equiv) (step 2) and NH$_3$ (7M in MeOH) (15 mL) were added into a 30 mL pressure tank reactor (10 atm). The resulting solution was stirred for 15 h at 100° C. The resulting mixture was concentrated under vacuum. The crude product was purified by Prep-HPLC with the following conditions: Column,)(Bridge Shield RP18 OBD Column, 5 μm, 19*150 mm; mobile phase, water (0.05% TFA) and ACN (31.0% ACN up to 42.0% in 10 min); Detector, UV 254/220 nm. This resulted in 400 mg (45%) of 6-chloro-2,3,4,9-tetrahydro-$^1$H-carbazole-1-carboxamide as a white solid.

$^1$H NMR (400 MHz, DMSO-d$_6$) δ: 10.81 (s, 1H), 7.44-7.36 (m, 2H), 7.29 (m, 1H), 7.10 (s, 1H), 7.00 (m, 1H), 3.66 (m, 1H), 2.64-2.56 (m, 2H), 2.11-1.89 (m, 3H), 1.70 (m, 1H). LC-MS: m/z=249 [M+H]$^+$.

Example 2:

6-chloro-1-deutero-2,3,4,9-tetrahydro-1H-carbazole-1-carboxamide (d$_1$-selisistat)

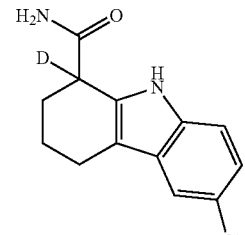

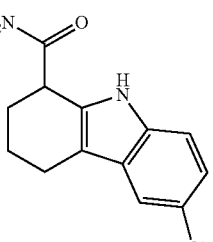

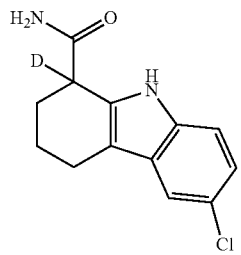

To a solution of 6-chloro-2,3,4,9-tetrahydro-$^1$H-carbazole-1-carboxamide (1 g, 4.0 mmol, 1.00 equiv) (Example 1, selisistat) in D$_2$O (10 mL) was added potassium carbonate (1.669 g, 12.1 mmol, 3.00 equiv). The resulting solution was stirred for 15 h at 100° C. The reaction mixture was cooled with a water bath. The resulting solution was extracted with ethyl acetate (3×20 mL). The organic layers were combined and washed with water (3×20 mL) and brine (3×20 mL). The mixture was dried over anhydrous sodium sulfate and concentrated under vacuum. The crude product was purified by Prep-HPLC with the following conditions: Column, XBridge Shield RP18 OBD Column, 5 μm, 19*150 mm; mobile phase, Water (0.05% TFA) and ACN (39.0% ACN up to 49.0% in 7 min); Detector, UV 254/220 nm. This resulted in 400 mg (40%) of 6-chloro-2,3,4,9-tetrahydro(1-$^2$H)-$^1$H-carbazole-1-carboxamide as a white solid.

$^1$H NMR (400 MHz, DMSO-d$_6$) δ: 10.81 (s, 1H), 7.44-7.41 (m, 2H), 7.29 (m, 1H), 7.12-7.07 (s, 1H), 7.00 (m, 1H), 2.61-2.58 (m, 2H), 2.05-1.98 (m, 3H), 1.78 (m, 1H). LC-MS: m/z=250 [M+H]$^+$.

Example 3

6-chloro-2,3,4,9-tetrahydro-1H-carbazole-2,2,3,3,4,4-d$_6$-1-carboxamide (d$_6$-selisistat)

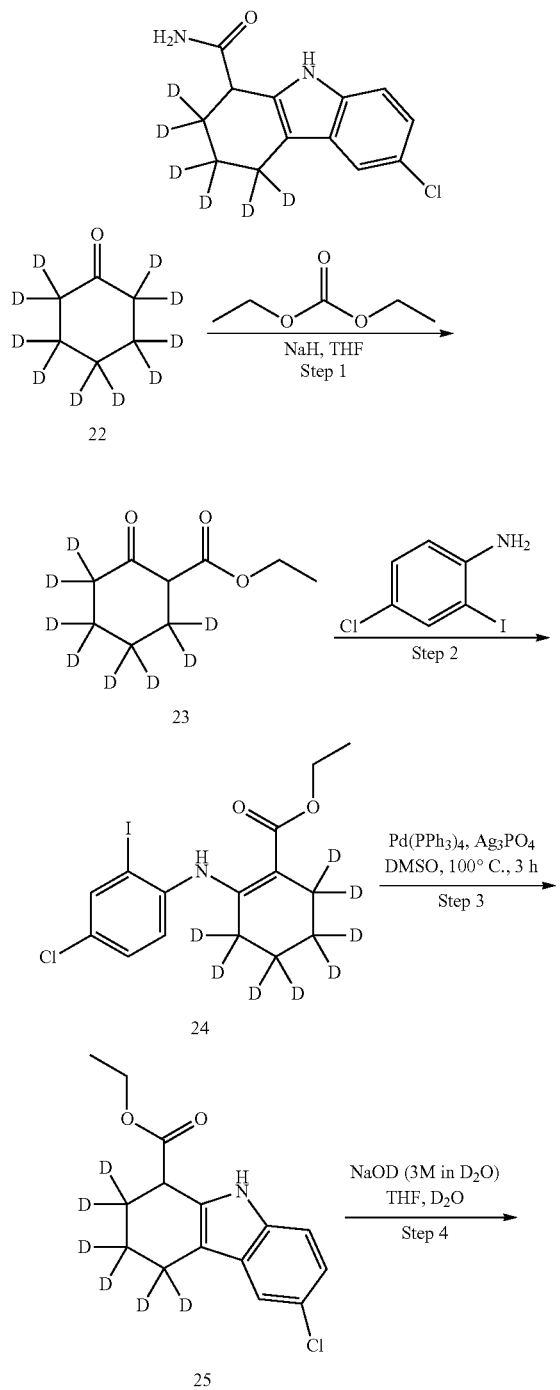

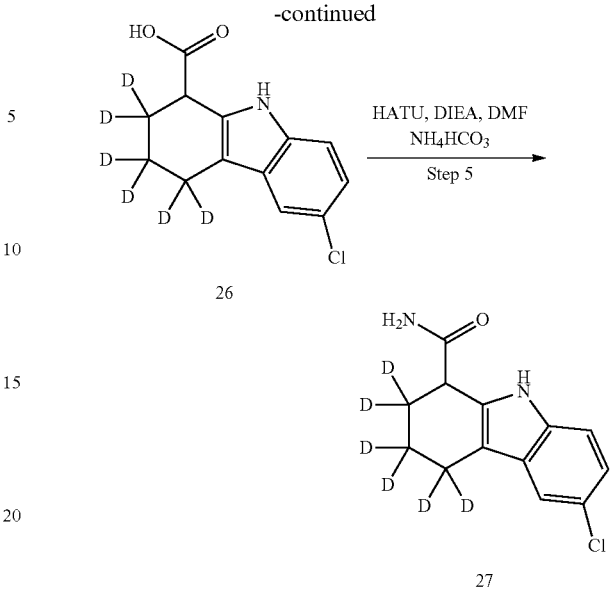

Step 1: ethyl 2-oxo($^2$H$_8$)cyclohexane-1-carboxylate

To a solution of diethyl carbonate (8.20 g, 66.90 mmol, 1.50 equiv) in tetrahydrofuran (60 mL) was added sodium hydride (2.45 g, 102.1 mmol, 2.20 equiv) in several portions. The resulting solution was stirred for 1 h at 65° C. To this was added ($^2$H$_{10}$)cyclohexan-1-one (5 g, 46.2 mmol, 1.00 equiv) dropwise with stirring at 65° C. in 30 min. The resulting solution was stirred for 1.5 h at 65° C. The reaction mixture was cooled. The reaction was then quenched by the addition of D$_2$O. The resulting solution was extracted with ethyl acetate (3×100 mL). The organic layers were washed with water (3×100 mL) and brine (3×100 mL). The mixture was dried over anhydrous sodium sulfate and concentrated under vacuum to afford 5 g (61%) of ethyl 2-oxo($^2$H$_8$)cyclohexane-1-carboxylate as yellow oil. LC-MS: m/z=179 [M+H]$^+$.

Step 2: ethyl 2-[(4-chloro-2-iodophenyl)amino]($^2$H$_8$)cyclohex-1-ene-1-carboxylate To a solution of ethyl 2-oxo($^2$H$_8$)cyclohexane-1-carboxylate (7 g, 39.27 mmol, 1.00 equiv) in ethanol (80 mL) was added AcOH (472 g, 7.86 mol, 0.20 equiv) and 4-chloro-2-iodoaniline (11.97 g, 47.22 mmol, 1.20 equiv). The resulting solution was stirred overnight at 25° C. The resulting mixture was concentrated under vacuum. The resulting solution was diluted with water (50 mL). The resulting solution was extracted with ethyl acetate (3×50 mL). The organic layers were washed with water (3×30 mL) and brine (3×30 mL). The mixture was dried over anhydrous sodium sulfate and concentrated under vacuum. The residue was applied onto a silica gel column eluting with petroleum ether to afford 2.6 g (16%) of ethyl 2-[(4-chloro-2-iodophenyl)amino]($^2$H$_8$)cyclohex-1-ene-1-carboxylate as yellow oil.

Step 3: ethyl 6-chloro-2,3,4,9-tetrahydro(2,2,3,3,4,4-$^2$H$_6$)$^1$H-carbazole-1-carboxylate To a solution of ethyl 2-[(4-chloro-2-iodophenyl)amino]($^2$H$_8$)cyclohex-1-ene-1-carboxylate (1.3 g, 3.14 mmol, 1.00 equiv) in DMSO (15 mL) was added Ag$_3$PO$_4$ (1.318 g, 3.14 mmol, 1.00 equiv) and Pd(PPh$_3$)$_4$ (48.97 mg, 0.04 mmol, 0.10 equiv). The resulting solution was stirred for 6 h at 100° C. The reaction mixture was cooled. The reaction was then quenched by the addition of D$_2$O (50 mL). The resulting solution was diluted with ethyl acetate (50 mL). The solids were filtered out. The filtrate was extracted with ethyl acetate (3×50 mL). The organic layers were washed with water (3×30 mL) and brine (3×30 mL). The mixture was dried over anhydrous sodium sulfate and concentrated under vacuum. The residue was applied onto a silica gel column with ethyl acetate/petroleum ether (1:10) to afford 400 mg (45%) of ethyl 6-chloro-2,3,4,9-tetrahydro(2,2,3,3,4,4-$^2$H$_6$)$^1$H-carbazole-1-carboxylate as a brown solid. LC-MS: m/z=284[M+H]$^+$.

Step 4: 6-chloro-2,3,4,9-tetrahydro(2,2,3,3,4,4-$^2$H$_6$)$^1$H-carbazole-1-carboxylic acid To a solution of ethyl 6-chloro-2,3,4,9-tetrahydro(2,2,3,3,4,4-$^2$H$_6$)$^1$H-carbazole-1-carboxylate (400 mg, 1.41 mmol, 1.00 equiv) in tetrahydrofuran (8 mL) and D$_2$O (2 mL) was added NaOD (3M in D$_2$O) (1.413 mL, 4.23 mmol, 3.00 equiv). The resulting solution was stirred for 5 h at 20° C. The pH value of the solution was adjusted to 3-4 with DCl (20% in D$_2$O). The resulting solution was extracted with ethyl acetate (3×30 mL). The organic layers were washed with water (3×20 mL) and brine (3×20 mL). The mixture was dried over anhydrous sodium sulfate and concentrated under vacuum to afford 360 mg (99.5%) of 6-chloro-2,3,4,9-tetrahydro(2,2,3,3,4,4-$^2$H$_6$)$^1$H-carbazole-1-carboxylic acid as a brown solid. LC-MS: m/z=256[M+H]$^+$.

Step 5: 6-chloro-2,3,4,9-tetrahydro(2,2,3,3,4,4-$^2$H$_6$)$^1$H-carbazole-1-carboxamide To a solution of 6-chloro-2,3,4,9-tetrahydro(2,2,3,3,4,4-$^2$H$_6$)$^1$H-carbazole-1-carboxylic acid (1.0 g, 4.0 mmol, 1.00 equiv) in N,N-dimethylformamide (15 mL) was added DIEA (756 mg, 5.8 mmol, 1.50 equiv), HATU (1.78 g, 4.6 mmol, 1.20 equiv), NH$_4$HCO$_3$ (617.2 mg, 7.8 mmol, 2.00 equiv). The resulting solution was stirred overnight at 25° C. The reaction was then quenched by the addition of D$_2$O. The resulting solution was extracted with ethyl acetate (3×20 mL). The organic layers were washed with water (3×10 mL) and brine (3×10 mL). The mixture was dried over anhydrous sodium sulfate and concentrated under vacuum. The crude product was purified by Prep-HPLC with the following conditions: Column, XSelect CSH Prep C18 OBD Column, 5 μm, 19*150 mm; mobile phase, Water (0.05% TFA) and ACN (40.0% ACN up to 40.0% in 7 min); Detector, UV 254/220 nm. This resulted in 200 mg (20%) of 6-chloro-2,3,4,9-tetrahydro(2,2,3,3,4,4-$^2$H$_6$)$^1$H-carbazole-1-carboxamide as a white solid.

$^1$H NMR (400 MHz, DMSO-d$_6$) δ: 10.80 (s, 1H), 7.40-7.38 (m, 2H), 7.29 (m, 1H), 7.09 (s, 1H), 7.00 (m, 1H), 3.65 (s, 1H). LC-MS: m/z=255 [M+H]$^+$.

Example 4:

6-chloro-1,2,2,3,3,4,4-tetradeutero-2,3,4,9-tetrahydro-1H-carbazole-1-carboxamide (d$_7$-selisistat)

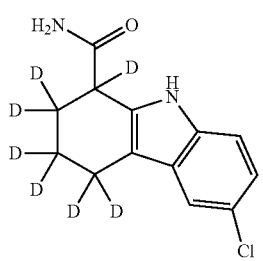

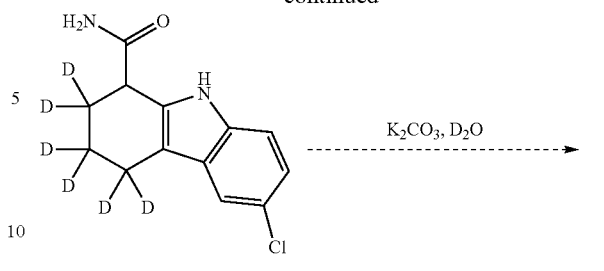

27

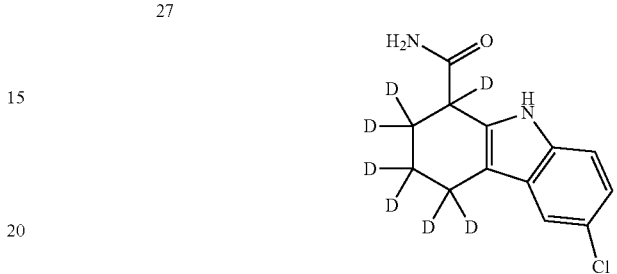

D$_7$-selisistat may be made by the method above. Isolation of enantiomers may be performed as in Example 1.

The following compounds, which are also within the scope of this disclosure, can generally be made using the methods described above in combination with methods known in the art.

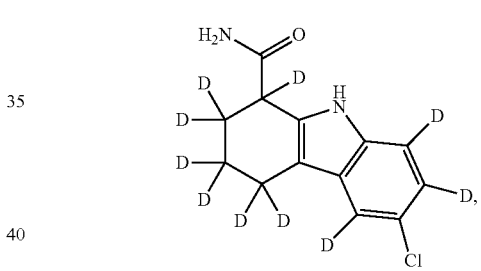

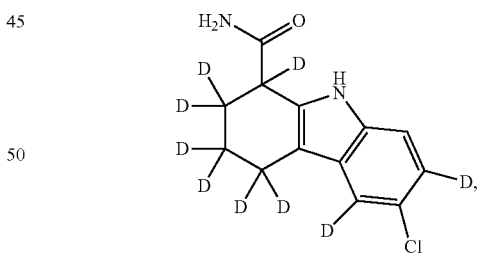

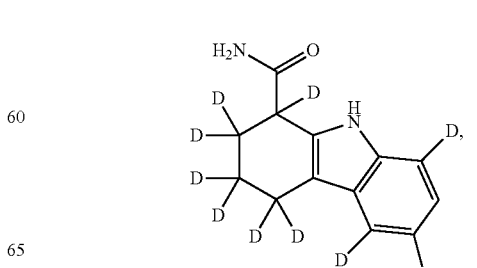

-continued
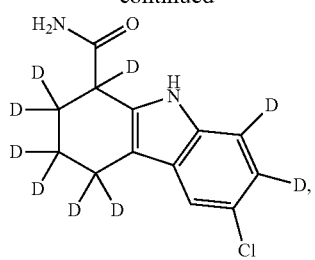
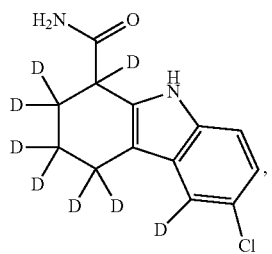
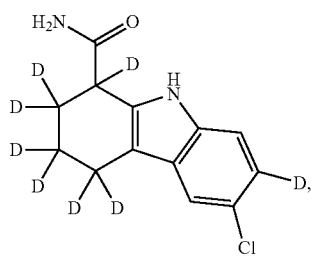
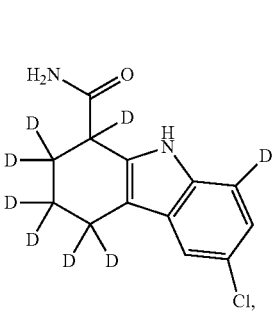
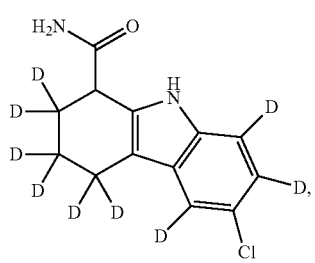
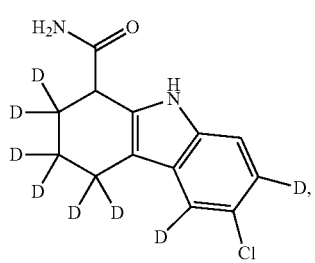
-continued
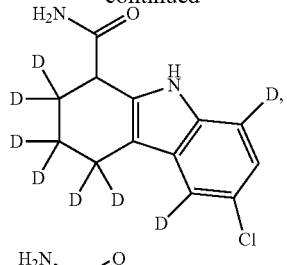
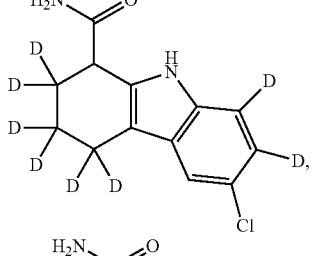
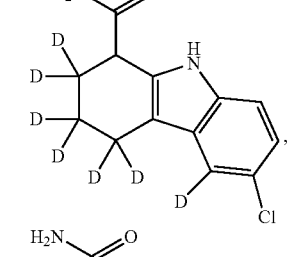
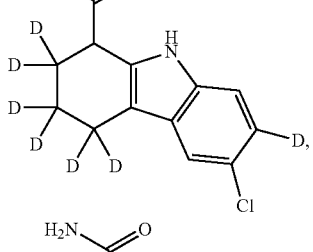
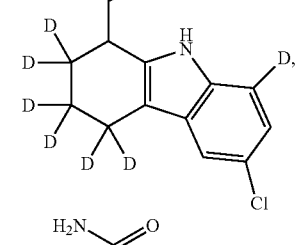
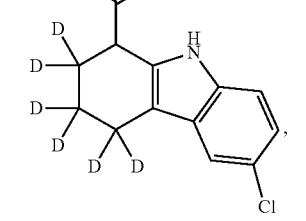
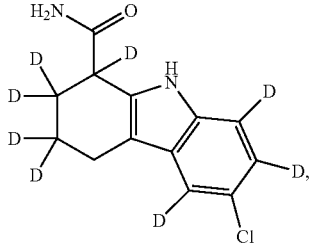

-continued
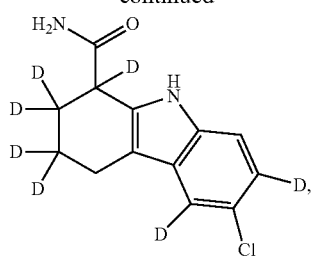
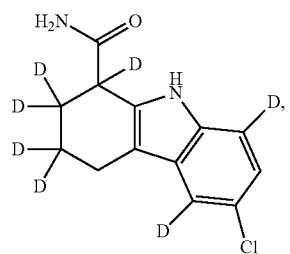
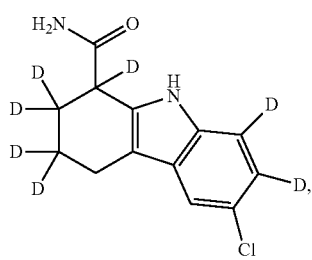
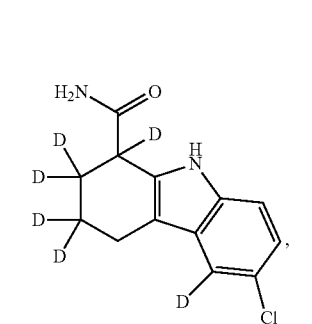
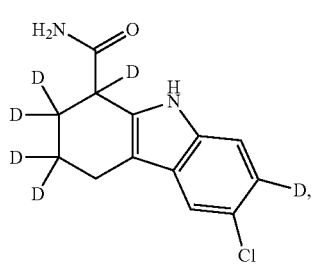
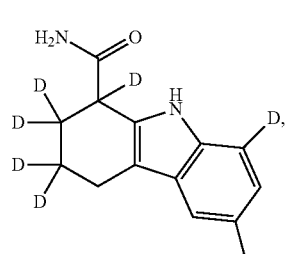
-continued
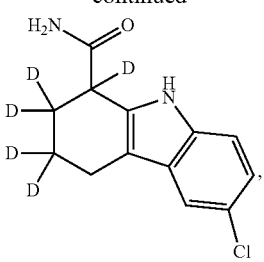
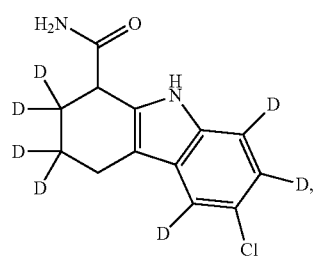
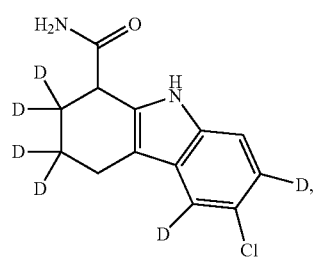
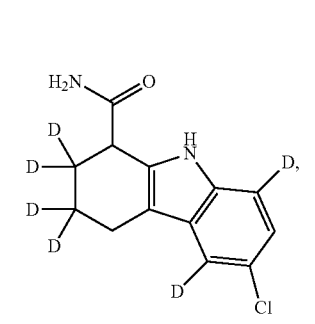
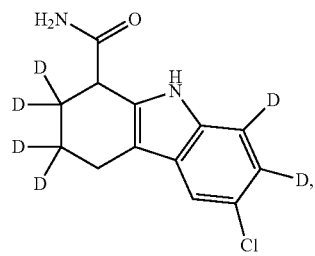
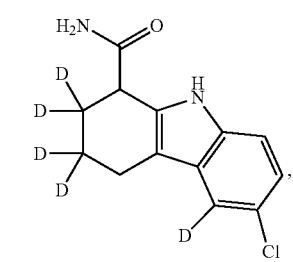

-continued
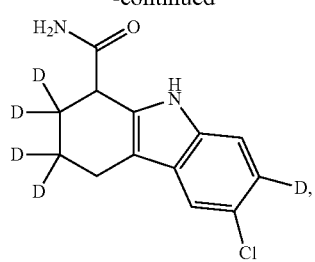
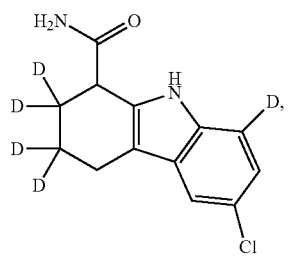
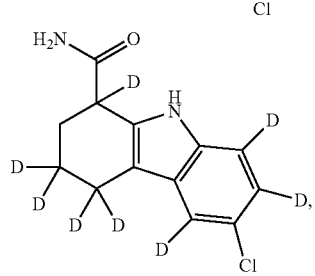
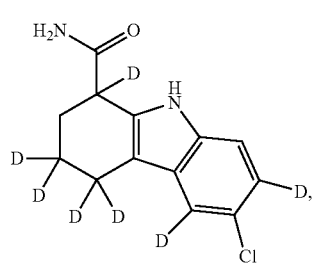
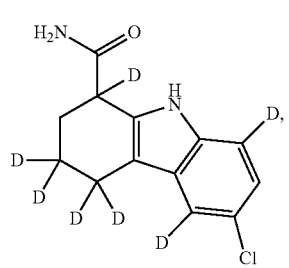
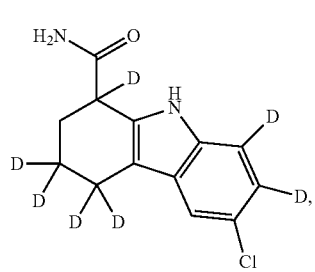
-continued
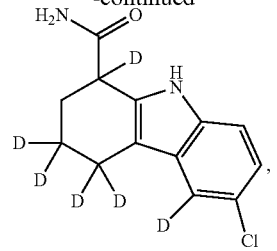
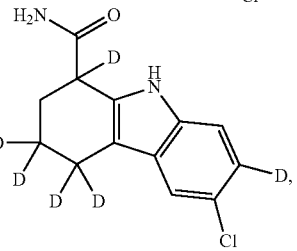
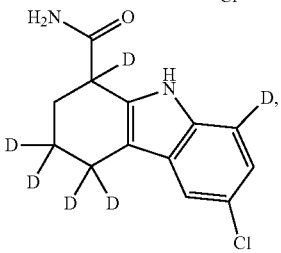
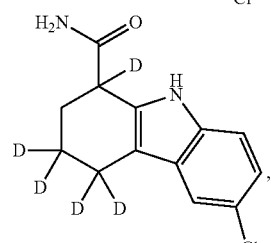
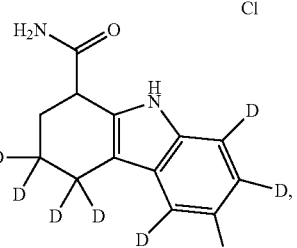
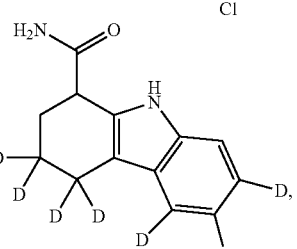
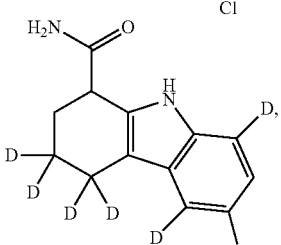

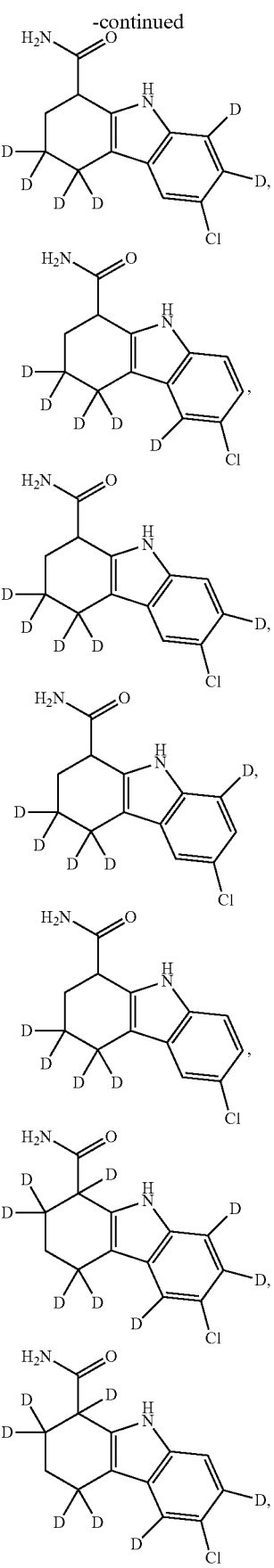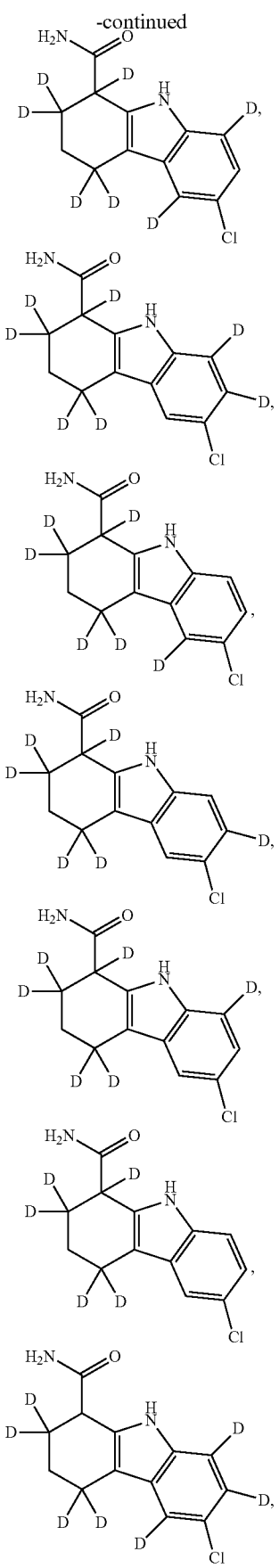

-continued
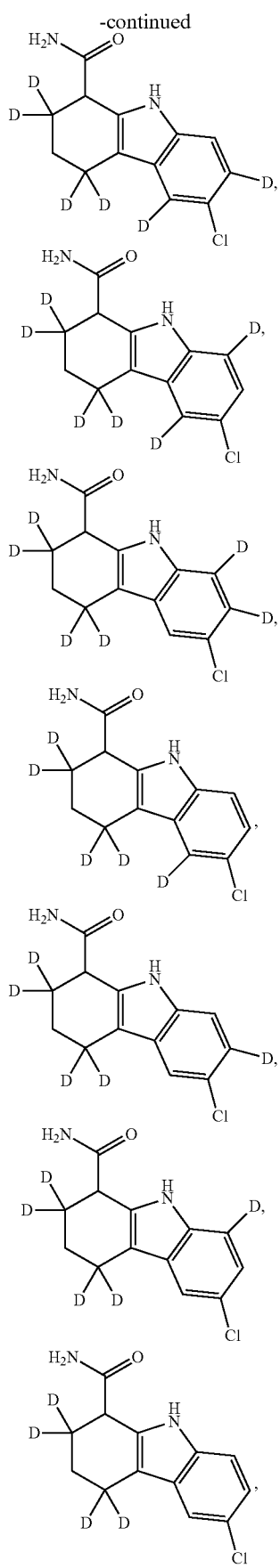
-continued
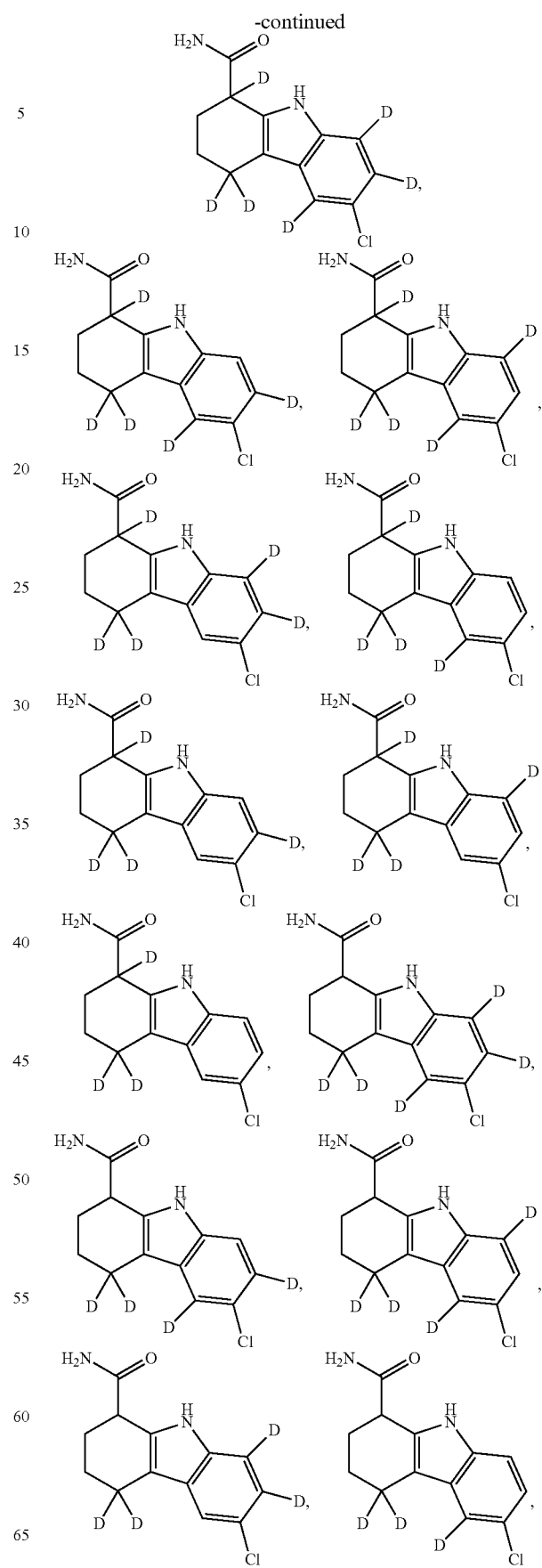

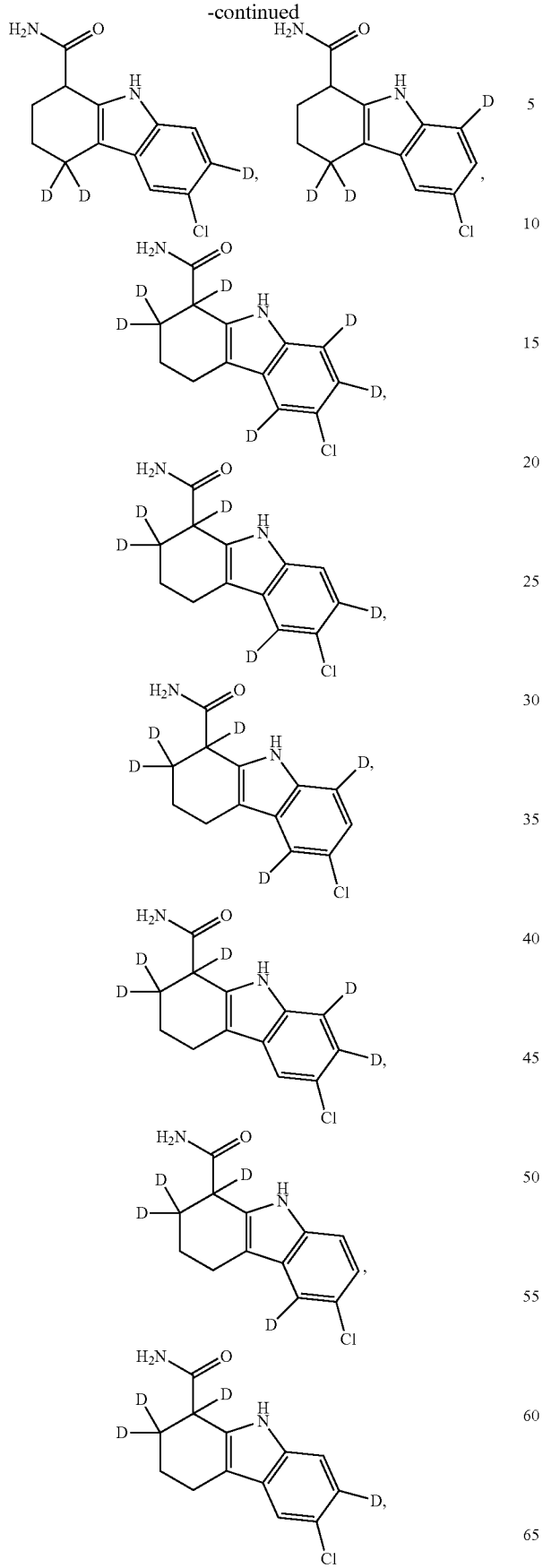
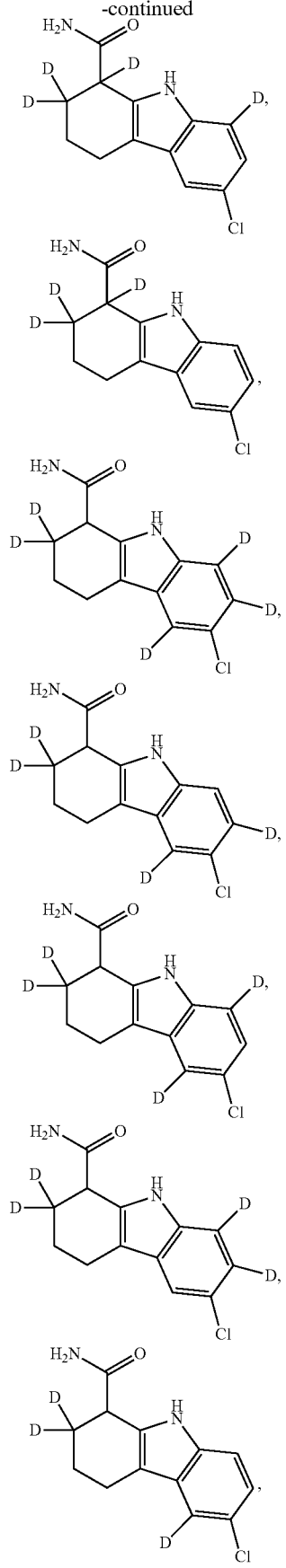

-continued
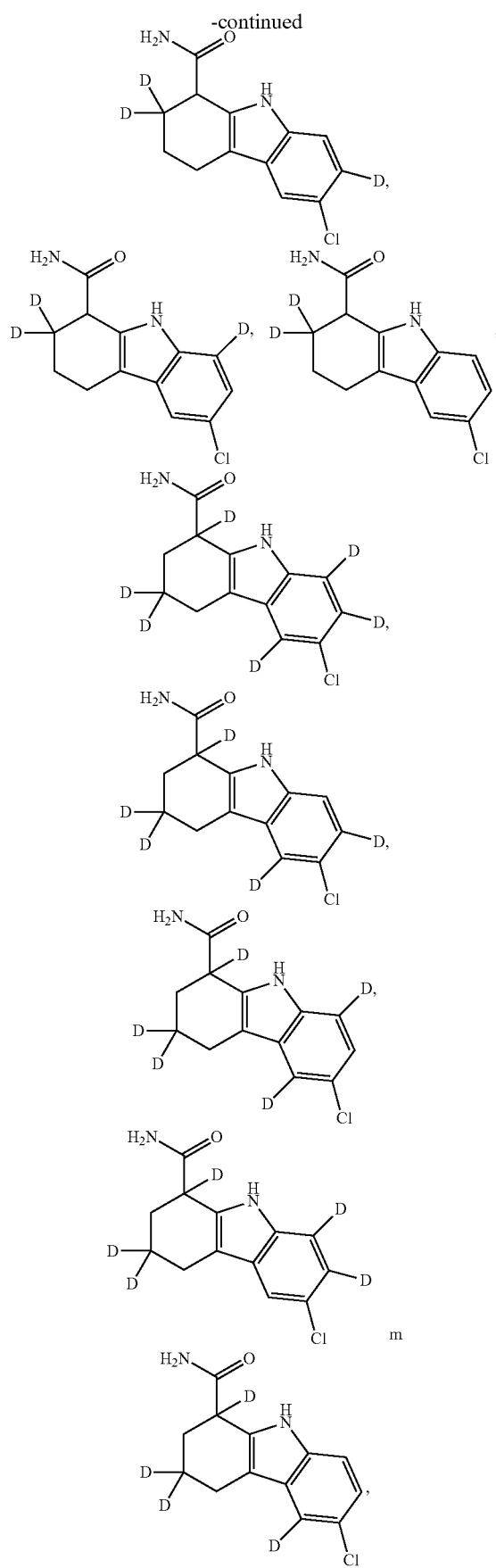
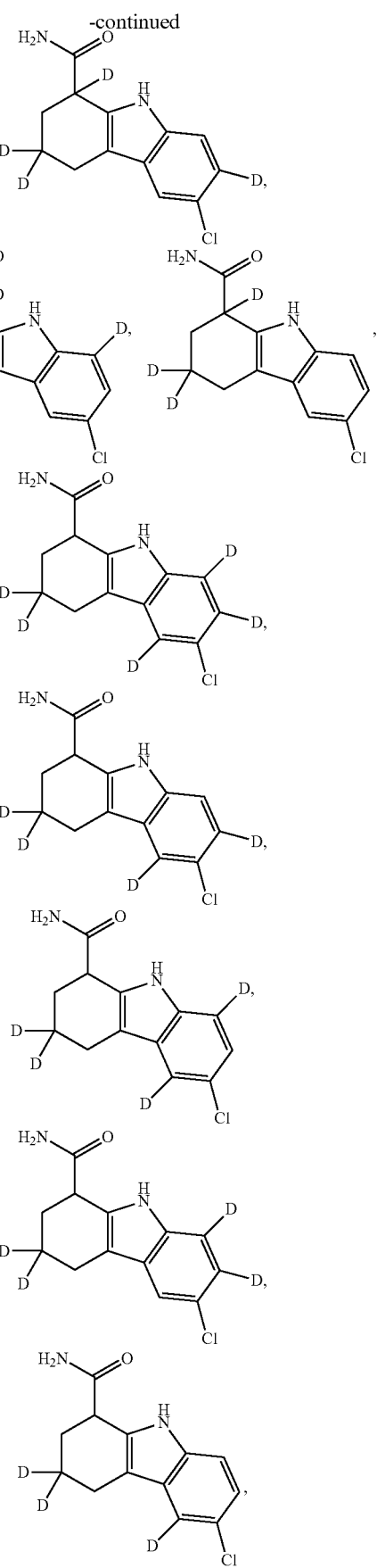

Changes in the metabolic properties of the compounds disclosed herein as compared to their non-isotopically enriched analogs can be shown using the following assays. Compounds listed above which have not yet been made and/or tested are predicted to have changed metabolic properties as shown by one or more of these assays as well.

Biological Activity Assays

In vitro Liver Microsomal Stability Assay

Human liver microsomal stability assays are conducted at 2 mg per mL liver microsome protein with an NADPH-generating system consisting of NADP (1 mM, pH 7.4), glucose-5-phosphate (5 mM, pH 7.4), and glucose-6-phosphate dehydrogenase (1 unit/mL). Test compounds were prepared as solutions in DMSO and added to the assay mixture (1 μM, final concentration in incubation) and were incubated at 37±1° C. Reactions were initiated with the addition of cofactor and were stopped at 0, 15, 30, 60, or 120 min after cofactor addition with stop reagent (0.2 mL acetonitrile). Samples were centrifuged (920×g for 10 min at 10° C.) in 96-well plates. Supernatant fractions were analyzed by LC-MS/MS to determine the percent remaining and estimate the degradation half-life of the test compounds. The results are presented in Table 1 below.

TABLE 1

| Sample # | Species | | Percent Remaining (%) | | | | | | $T_{1/2}$ (minute) | $Cl_{int}$ (mL/min/kg) |
|---|---|---|---|---|---|---|---|---|---|---|
| | | | 0 min | 15 min | 30 min | 60 min | 120 min | 120 min w/o NADPH min | | |
| Ketanserin | Human | Mean | 100 | 78.08 | 64.73 | 44.75 | 26.52 | 97.70 | 43.58 | 39.88 |
| | | RSD of Area Ratio | n/a | 0.02 | 0.07 | 0.09 | n/a | 0.06 | | |
| Example 1 | Human | Mean | 100 | 93.37 | 90.46 | 73.66 | 52.94 | 102.02 | 128.00 | 13.58 |
| | | RSD of Area Ratio | 0.02 | 0.03 | 0.03 | 0.06 | 0.03 | 0.01 | | |
| Example 2 | Human | Mean | 100 | 100.12 | 85.44 | 71.84 | 59.95 | 100.36 | 152.09 | 11.43 |
| | | RSD of Area Ratio | 0.04 | 0.07 | 0.03 | 0.10 | 0.11 | 0.03 | | |
| Example 3 | Human | Mean | 100 | 92.39 | 86.96 | 70.69 | 52.83 | 96.74 | 128.35 | 13.54 |
| | | RSD of Area Ratio | 0.08 | 0.03 | 0.04 | 0.06 | 0.05 | 0.02 | | |

In vitro metabolism using human cytochrome $P_{450}$ enzymes

The cytochrome $P_{450}$ enzymes were expressed from the corresponding human cDNA using a baculovirus expression system (BD Biosciences, San Jose, Calif.). A 0.25 milliliter reaction mixture containing 0.8 milligrams per milliliter protein, 1.3 millimolar $NADP^+$, 3.3 millimolar glucose-6-phosphate, 0.4 U/mL glucose-6-phosphate dehydrogenase, 3.3 millimolar magnesium chloride and 0.2 millimolar of a compound of Formula I, the corresponding non-isotopically enriched compound or standard or control in 100 millimolar potassium phosphate (pH 7.4) was incubated at 37° C. for 20 min. After incubation, the reaction was stopped by the addition of an appropriate solvent (e.g., acetonitrile, 20% trichloroacetic acid, 94% acetonitrile/6% glacial acetic acid, 70% perchloric acid, 94% acetonitrile/6% glacial acetic acid) and centrifuged (10,000 g) for 3 min. The supernatant was analyzed by HPLC/MS/MS.

| Cytochrome $P_{450}$ | Standard |
|---|---|
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |
| CYP2C19 | [$^{13}$C]-(S)-mephenytoin |
| CYP2D6 | (+/−)-Bufuralol |
| CYP2E1 | Chlorzoxazone |
| CYP3A4 | Midazolam |
| CYP4A | [$^{13}$C]-Lauric acid |

The results are presented in Table 2 below.

TABLE 2

| Sample # | | Species | Percent Remaining (%) | | | | | $T_{1/2}$ (minute) | $Cl_{int}$ (mL/min/pmol) |
|---|---|---|---|---|---|---|---|---|---|
| | | | 0 min | 15 min | 30 min | 45 min | 60 min | | |
| Phenacetin | Cyp 1A2 | Mean | 100.00 | 53.02 | 31.01 | 20.20 | 15.08 | 19.49 | 0.00018 |
| | | RSD of Area Ratio | 0.03 | 0.01 | 0.02 | 0.06 | 0.02 | | |
| Midazolam | Cyp 3A4 | Mean | 100.00 | BQL | BQL | BQL | BQL | <5 | >0.0014 |
| | | RSD of Area Ratio | 0.00 | N/A | N/A | N/A | N/A | | |
| Example 1 | Cyp 1A2 | Mean | 100.00 | 46.28 | 24.21 | 16.02 | 11.55 | 16.92 | 0.00020 |
| | | RSD of Area Ratio | 0.03 | 0.02 | 0.05 | 0.07 | 0.06 | | |
| | Cyp 3A4 | Mean | 100.00 | 63.43 | 55.02 | 54.21 | 51.13 | 52.52 | 0.00013 |
| | | RSD of Area Ratio | 0.03 | 0.03 | 0.01 | 0.05 | 0.02 | | |
| Example 2 | Cyp 1A2 | Mean | 100.00 | 48.53 | 27.30 | 17.05 | 12.99 | 17.67 | 0.00020 |
| | | RSD of Area Ratio | 0.02 | 0.07 | 0.02 | 0.03 | 0.07 | | |
| | Cyp 3A4 | Mean | 100.00 | 69.07 | 59.14 | 54.63 | 53.05 | 52.79 | 0.00013 |
| | | RSD of Area Ratio | 0.02 | 0.00 | 0.02 | 0.05 | 0.04 | | |
| Example 3 | Cyp 1A2 | Mean | 100.00 | 45.84 | 26.01 | 17.34 | 12.82 | 17.85 | 0.00019 |
| | | RSD of Area Ratio | 0.04 | 0.04 | 0.04 | 0.07 | 0.07 | | |
| | Cyp 3A4 | Mean | 100.00 | 69.80 | 61.49 | 63.89 | 60.39 | 70.68 | 0.00010 |
| | | RSD of Area Ratio | 0.00 | 0.03 | 0.08 | 0.03 | 0.07 | | |

Monoamine Oxidase A Inhibition and Oxidative Turnover

The procedure is carried out using the methods described by Weyler, *Journal of Biological Chemistry* 1985, 260, 13199-13207, which is hereby incorporated by reference in its entirety. Monoamine oxidase A activity is measured spectrophotometrically by monitoring the increase in absorbance at 314 nm on oxidation of kynuramine with formation of 4-hydroxyquinoline. The measurements are carried out, at 30° C., in 50 mM $NaP_i$ buffer, pH 7.2, containing 0.2% Triton X-100 (monoamine oxidase assay buffer), plus 1 mM kynuramine, and the desired amount of enzyme in 1 mL total volume.

Monooamine Oxidase B Inhibition and Oxidative Turnover

The procedure is carried out as described in Uebelhack, *Pharmacopsychiatry* 1998, 31(5), 187-92, which is hereby incorporated by reference in its entirety.

SIRT1 Activity Assays

SIRT1 activity may be assessed using any known technique, including via commercially available assays. One example of a SIRT1 assay is available from Sigma Aldrich and employs a two-step enzymatic reaction in which a substrate that contains an acetylated lysine side chain is deacetylated by SIRT1 and a developing solution cleaves the deacetylated substrate and releases a highly fluorescent group. The measured fluorescence is directly proportional to the deacetylation activity of the enzyme in the sample and is reported in comparison to an inhibitor (e.g., nicotinamide) as negative control and an activator (e.g., resveratrol) as positive control. Other fluorometric assays, operating on similar principles and optionally varying the substrate, developing chemicals, controls, etc. are available from other suppliers.

Murine Model of Huntington's Disease

Among transgenic mouse models, the R6/2 mouse represents one of the most widely employed and characterized in vivo models for preclinical studies and has been the model of choice for a variety of pharmacological preclinical trials. The R6/2 mouse expresses a human exon 1 fragment encoding an expanded polyglutamine repeat under control of the human Htt promoter and displays rapid symptomatic onset and robust disease progression. This model is characterized, among other phenotypes, by decreased survival, loss of body weight, impaired motor activity, striatal degeneration and the presence of Htt-positive aggregates in the brain and other tissues.

Compounds disclosed herein may be administered to transgenic R6/2 mice beginning at 4.5 weeks of age to death at doses of, e.g., 5 and 20 mg/kg. The animals are then subjected to a battery of standardized, disease-relevant phenotypic tests. Treatment is expected to result in increased survival; improvements in voluntary locomotor activity (Open Field parameters), especially amelioration of deficits of R6/2 mice detected both in distance travelled in the center and average velocity in the Open Field; and increase in body weight.

The effects of compounds on brain pathology may be analyzed in a satellite group of animals that is sacrificed at 12 weeks of age (8 weeks of treatment). Ventricular volume and EM48 (Htt)-positive staining of aggregates are investigated as measures of striatal degeneration and Htt aggregate load, respectively. HD-like pathological indicators in R6/2 mice mimic those seen in HD patients in the loss of striatal tissue with an associated increase in ventricular volume and accumulation of EM48-positive inclusions in the brain. Treatment is expected to result in reduction of ventricular volume in comparison with vehicle-treated animals. Brain slices may be examined for the presence of inclusions of EM48-positive aggregates in vehicle- and compound-treated animals using automated image analysis. A decrease in the number of inclusions is expected to be observed in treated animals. See, e.g., Smith et al., Human Molecular Genetics, 2014, Vol. 23, No. 11 2995-3007.

Murine MOG-EAE Model of Multiple Sclerosis

EAE is induced in 10-wk-old female B6 WT and $SIRT1^{-/-}$ mice by subcutaneous immunization with $MOG_{35-55}$ peptide in complete Freund's adjuvant, followed by pertussis toxin injection on days 0 and 2 of the immunization intraperitoneally (Davalos et al., 2012). To examine compound effect on EAE induction, either DMSO or compound (e.g., at 10 mg/kg) are subcutaneously injected on day 0, 1, and 2 after EAE induction. Mice are scored daily as follows: 0, no symptoms; 1, loss of tail tone; 2, ataxia; 3, hind limb paralysis; 4, hind limb and fore limb paralysis; 5, moribund. Experiments are performed in a blinded manner to the genotypes in two separate mouse cohorts. Data are represented as the mean clinical score with error bars (±SEM), and the Mann-Whitney U test is used for statistical analysis using PRISM software.

Histopathological analysis is performed on paraffin sections. Sections are stained with hematoxylin/eosin or luxol fast blue/periodic acid-Schiff Images may be acquired, e.g., with an Axioplan II epifluorescence microscope (Carl Zeiss, Inc.) equipped with dry Plan-Neofluar objectives (10×0.3 NA, 20×0.5 NA, or 40×0.75 NA). Number of inflammatory foci and demyelinated area are quantified using ImageJ (National Institutes of Health) by a blinded observer as described previously (Adams et al., 2007).

Human Pharmacokinetic Study of SIRT1 Inhibitors

The safety, tolerability, pharmacokinetics, etc. may be assessed in human volunteers as disclosed in Westerberg G et al., "Safety, pharmacokinetics, pharmacogenomics and QT concentration-effect modelling of the SIRT1 inhibitor selisistat in healthy volunteers," *Br J Clin Pharmacol*. 2015, 79(3):477-91, which is hereby incorporated by reference in its entirety.

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

From the foregoing description, one skilled in the art can easily ascertain the essential characteristics of this disclosure, and without departing from the spirit and scope thereof, can make various changes and modifications of the disclosure to adapt it to various usages and conditions.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications

What is claimed is:

1. A compound of Formula III:

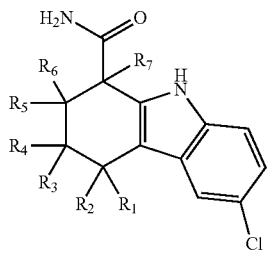

(III)

or a salt, prodrug, or solvate thereof, wherein:
$R_1$-$R_7$ are, independently, hydrogen or deuterium;
at least one of $R_1$-$R_7$ is deuterium; and
at least one of $R_1$-$R_7$ has deuterium enrichment of no less than about 10%.

2. The compound of claim 1, wherein $R_1$, $R_2$, $R_3$, $R_4$, $R_5$, and $R_6$ are deuterium.

3. The compound of claim 1, wherein $R_7$ is deuterium.

4. The compound of claim 1, wherein $R_1$, $R_2$, $R_3$, $R_4$, $R_5$, $R_6$, and $R_7$ are deuterium.

5. The compound of claim 1, wherein at least one of $R_1$-$R_7$ has deuterium enrichment of no less than about 50%.

6. The compound of claim 1, wherein at least one of $R_1$-$R_7$ has deuterium enrichment of no less than about 90%.

7. The compound of claim 1, wherein at least one of $R_1$-$R_7$ has deuterium enrichment of no less than about 98%.

8. The compound of claim 1, wherein the compound is:

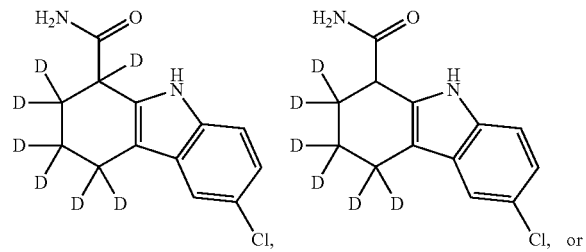

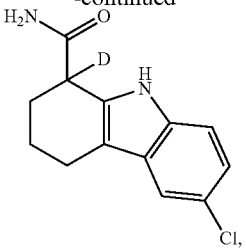

or a salt, prodrug, or solvate thereof.

9. The compound of claim 8, which is:

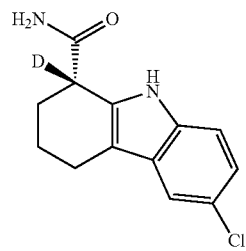 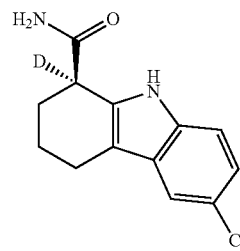

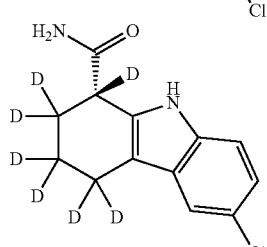 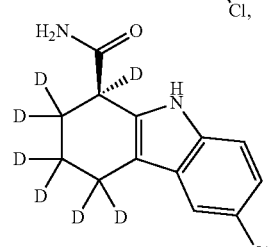

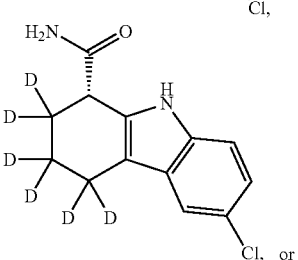 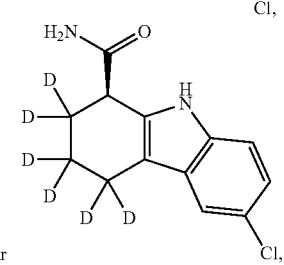

or a salt, prodrug, or solvate thereof.

10. The compound of claim 8, wherein each position represented as D has deuterium enrichment of no less than about 10%.

11. The compound of claim 10, wherein each position represented as D has deuterium enrichment of no less than about 50%.

12. The compound of claim 11, wherein each position represented as D has deuterium enrichment of no less than about 90%.

13. The compound of claim 12, wherein each position represented as D has deuterium enrichment of no less than about 98%.

14. A pharmaceutical composition comprising a compound of claim 1 and a pharmaceutically acceptable carrier.

* * * * *